(12) United States Patent
Hocker et al.

(10) Patent No.: US 10,310,493 B2
(45) Date of Patent: Jun. 4, 2019

(54) SYSTEM AND METHOD FOR ASSESSMENT OF A WORKPIECE IN A CONTINUOUS FLOW PROCESS

(71) Applicant: John Bean Technologies Corporation, Chicago, IL (US)

(72) Inventors: Jon A. Hocker, Bothell, WA (US); George R. Blaine, Lake Stevens, WA (US); Craig E. Pfarr, Issaquah, WA (US)

(73) Assignee: John Bean Technologies Corporation, Chicago, IL (US)

(*) Notice: Subject to any disclaimer, the term of this patent is extended or adjusted under 35 U.S.C. 154(b) by 365 days.

(21) Appl. No.: 15/174,910

(22) Filed: Jun. 6, 2016

(65) Prior Publication Data
US 2017/0108855 A1    Apr. 20, 2017

Related U.S. Application Data

(60) Provisional application No. 62/242,900, filed on Oct. 16, 2015.

(51) Int. Cl.

| | |
|---|---|
| *G01N 3/42* | (2006.01) |
| *A22C 17/00* | (2006.01) |
| *A22C 21/00* | (2006.01) |
| *G01N 33/12* | (2006.01) |
| *G05B 23/02* | (2006.01) |
| *G05B 19/042* | (2006.01) |

(52) U.S. Cl.
CPC ...... *G05B 23/0205* (2013.01); *A22C 17/0006* (2013.01); *A22C 17/008* (2013.01); *A22C 17/0086* (2013.01); *A22C 21/0023* (2013.01); *A22C 21/0053* (2013.01); *G01N 3/42* (2013.01); *G01N 33/12* (2013.01); *G05B 19/0428* (2013.01); *G05B 2219/31274* (2013.01); *G05B 2219/40554* (2013.01)

(58) Field of Classification Search
CPC .................................................. G05B 23/0205
See application file for complete search history.

(56) References Cited

U.S. PATENT DOCUMENTS

| | | | |
|---|---|---|---|
| 5,585,603 A | 12/1996 | Vogeley, Jr. | |
| 9,149,058 B2 * | 10/2015 | Bilet | A47J 27/16 |

(Continued)

FOREIGN PATENT DOCUMENTS

| | | | |
|---|---|---|---|
| EP | 0916947 | * | 11/1997 |
| EP | 0 916 947 A1 | | 5/1999 |

OTHER PUBLICATIONS

Rocchini, C., et al., "A Low Cost 3D Scanner Based on Structured Light," Computer Graphics Forum 20(3):299-308, Sep. 2001.

(Continued)

*Primary Examiner* — Manuel L Barbee
*Assistant Examiner* — Raymond L Nimox
(74) *Attorney, Agent, or Firm* — Christensen O'Connor Johnson Kindness PLLC

(57) ABSTRACT

A system for measuring physical properties of a workpiece in motion which includes a conveyance assembly for conveying the workpiece, a scanning assembly for scanning the workpiece, and a measurement assembly for measuring at least one physical property of the workpiece while the workpiece is in motion.

22 Claims, 16 Drawing Sheets

(56) References Cited

U.S. PATENT DOCUMENTS

| | | | |
|---|---|---|---|
| 2004/0231480 A1* | 11/2004 | Wattles | A22C 17/0093 83/401 |
| 2005/0032471 A1* | 2/2005 | Pfarr | B23K 26/0838 452/181 |
| 2009/0038455 A1* | 2/2009 | Strong | B23D 47/045 83/155.1 |
| 2014/0220193 A1* | 8/2014 | Hocker | G01K 13/00 426/231 |
| 2015/0205288 A1 | 7/2015 | Strong et al. | |

OTHER PUBLICATIONS

International Search Report and Written Opinion dated Jan. 25, 2017, issued in corresponding International Application No. PCT/US2016/057013, filed Oct. 14, 2016, 12 pages.

* cited by examiner

SYSTEM AND METHOD FOR ASSESSMENT OF A WORKPIECE IN A CONTINUOUS FLOW PROCESS

CROSS-REFERENCE TO RELATED APPLICATION

This application claims the benefit of U.S. Provisional Patent Application No. 62/242,900, filed Oct. 16, 2015, which is incorporated herein by reference in its entirety.

FIELD OF THE INVENTION

The present invention relates generally to a system and method for assessing the physical properties of a workpiece in motion, and optionally processing the workpiece with a cutting assembly, and/or sorting, and/or optionally unloading the workpieces while in motion in response to measured physical properties of the workpiece.

BACKGROUND OF THE INVENTION

Workpieces, such food products, often vary in physical properties. The variation in physical properties may be economically significant from piece to piece. More specifically, the value and end use of a workpiece may depend in whole or in part upon the physical properties of the workpiece. In the case of a food product, tenderness, texture, stiffness, time dependent strain, resilience, or other physical properties are commercially important measures of quality.

Food products are often processed in motion on a conveyor system. Thus, any scanning, measurements, and other processing (cutting, trimming, slicing, etc.) must occur while the workpiece is in motion. After any preliminary processing occurs, the workpieces must also be unloaded, transferred, purposefully left on the conveyor, or moved into a desired location for subsequent processing, such as marinating, breading, cooking, cooling, packaging, etc.

Processing a food product or other workpiece while it is in motion presents many challenges. For instance, in some applications, the apparatus that is processing the workpiece may need to move along with the workpiece while performing the processing step. In addition thereto or in the alternative, the apparatus must process the workpiece so quickly that the motion of the workpiece is uninterrupted. Moreover, the workpiece must be processed quickly to ensure that it is finished before subsequent processing occurs.

In the specific example of a food product such as chicken, the chicken may be scanned to determine its shape and size, it may be sorted based upon product attributes, it may be portioned or cut into a desired shape or size (before or after sorting), and it may be off-loaded for further processing. Technology exists for scanning, sorting, portioning trimming, and/or unloading a food product such as chicken while on a moving conveyor system. An example of such a system is shown and described in U.S. Patent Application Publication No. 20150205288, entitled "System for Cutting and Unloading Portions", filed on Jan. 22, 2014, the disclosure of which is hereby incorporated by reference in its entirety.

However, it would also be useful to test and assess the physical properties of a workpiece in motion to determine the quality and/or use of the workpiece. As an example, certain pieces of chicken breasts may be suitably tender for consumption without the need for significant processing, while other pieces may only be suitable after further processing, such as brining, tenderizing, etc. Moreover, certain pieces may be so poor in quality that they must be discarded.

For instance, white striping and hard or "woody" texture has been observed in some chicken breast muscles. This chicken product, referred to as "woody chicken," is leading to customer complaints. The woody chicken is typically a very stiff meat that can be used in limited applications, or perhaps not used at all. Thus, a need exists for testing and assessing the physical properties of a workpiece, such as the viscoelastic or resilience properties of chicken breasts, while the workpiece is in motion, for determining the end use of the chicken and/or for identifying workpieces that must be discarded. The unit of resilience can be calculated, for example, using the area beneath a measured stress-strain ($\sigma$-$\epsilon$) curve.

Current technology exists in lab, table top or batch format to assess fruit quality or meat tenderness. Typically these lab systems employ fixtures that have a long cycle time (e.g., about 1 minute per piece), and the fixtures destroy the workpiece during the test. Moreover, the lab fixtures are not suitable to test the workpieces as they are moving.

Moreover, it should be appreciated that the temperature of the workpiece may affect its measured viscoelastic properties. For instance, a chicken breast that is frozen (100% ice crystals) will be significantly stiffer than a chicken breast that is partially frozen (in the latent zone) or thawed (0% ice crystals). Thus, a further need may exist for measuring and accounting for the temperature or energy content of the workpiece in motion when assessing the physical properties of a workpiece in motion.

The present invention automates the physical assessment of workpieces, such as chicken breasts, in a non-destructive, 100% inspection, high-speed, continuous flow system. More specifically, in one aspect, the present invention involves scanning the workpiece to identify one or more region of interests, guiding a measurement system to a region of interest, measuring physical attributes at the region of interest on the workpiece while the workpiece is in motion, and recording the measured information for the selected workpiece for subsequent use and optionally acting upon the measured information. In another aspect, the present invention involves scanning the workpiece to identify one or more region of interests, measuring physical attributes at a region of interest on the workpiece while the workpiece is in motion, and recording the measured information for the selected workpiece for subsequent use and optionally acting upon the measured information.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, a system for measuring physical properties of a workpiece in motion includes a conveyance assembly for conveying the workpiece, a scanning assembly for scanning the workpiece, and a measurement assembly for measuring at least one physical property of the workpiece while the workpiece is in motion. In another aspect, the system includes a first carrier unit for moving the measurement assembly relative to the conveyance assembly to measure the workpiece while the workpiece is in motion.

In yet another aspect, the measurement assembly is a rotary actuator configured to selectively move an impact device into and out of engagement with the workpiece. In a further aspect, the impact device is coupled to an output shaft of the rotary actuator, wherein an axis of the output shaft is substantially transverse to an axis of the impact device, and wherein the axis of the output shaft is substantially parallel to a longitudinal axis of the conveyance assembly.

In another aspect, a system for measuring physical properties of a workpiece in motion may comprise a conveyance assembly for conveying the workpiece, a scanning assembly for scanning the workpiece, a measurement assembly for precisely measuring time-dependent strain of a viscoelastic workpiece, a cutting assembly for cutting portions from the workpiece, an optional unloading system operably operable to remove the cut portions from the conveyance assembly, and a carrier assembly for moving the measuring, cutting and unloading assemblies relative to the conveyance assembly to measure and to optionally cut and/or unload the workpieces from the conveyance assembly. The system further includes a control system processor operable to process the scanning data, compare measured physical attribute data to allowed physical attribute limits, and portion specification settings to determine what use and optionally what cutting paths are required to achieve a desired product type, shape and/or size portions from the workpiece. The control system directs the measurement system to perform the required physical attribute measurements, optionally directs the cutting system to perform the required cuts, and optionally directs the unloading system to pick up the cut or whole portions and deposit the portions at desired locations based on the known location of the portions, as determined in the scanning, measuring, and cutting steps.

In another aspect, and as generally illustrated in FIG. 16, a method of processing a workpiece in motion based on measured physical properties of the workpiece includes moving at least one workpiece along a conveyance assembly, scanning the workpiece to determine a workpiece region of interest, measuring a physical property of the at least one workpiece at the region of interest while the workpiece is in motion, comparing the measurement data to predetermined criteria, and selecting a subsequent processing step for the at least one workpiece based upon said comparison. The physical property of the workpiece may include time dependent strain.

DESCRIPTION OF THE DRAWINGS

The foregoing aspects and many of the attendant advantages of this invention will become more readily appreciated by reference to the following detailed description, when taken in conjunction with the accompanying drawings, wherein.

DETAILED DESCRIPTION

The detailed description set forth below in connection with the appended drawings, where like numerals reference like elements, is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the disclosure to the precise forms disclosed. Similarly, any steps described herein may be interchangeable with other steps, or combinations of steps, in order to achieve the same or substantially similar result.

In the following description, numerous specific details are set forth in order to provide a thorough understanding of exemplary embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein.

The present application includes references to directions, such as "forward," "rearward," "upward," "downward," "extended," "advanced," and "retracted." These references and other similar references in the present application are only to assist in helping describe and understand the present invention and are not intended to limit the present invention to these directions. Also, references to "workpiece," "workpiece," "food product," "food piece," "portion" are understood to be interchangeable and are not meant to be limiting in nature.

Figure 1:
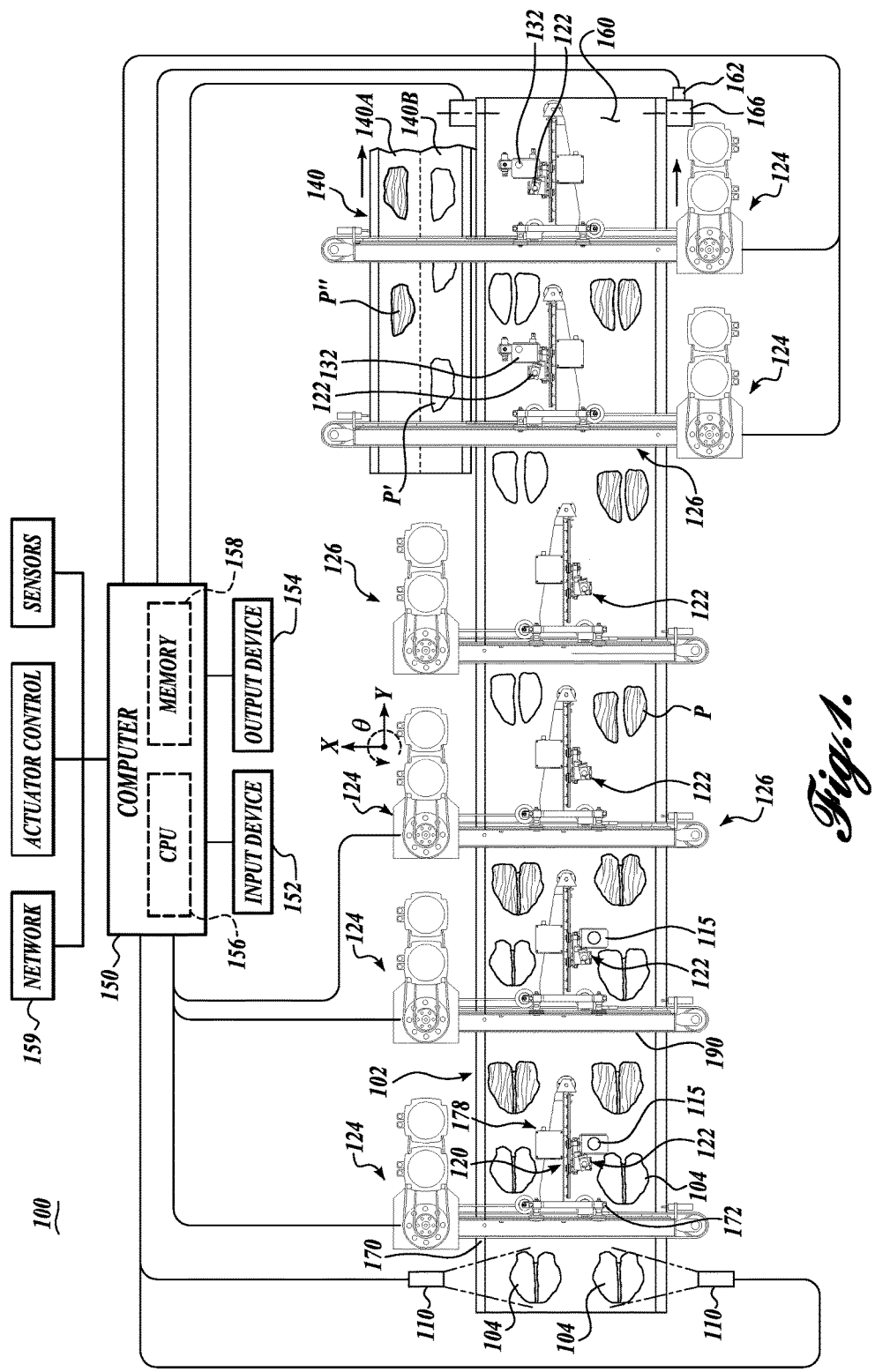
FIG. 1 is a top schematic view of a first exemplary embodiment of a system formed in accordance with the present disclosure that is configured for measuring physical attributes and optionally cutting and/or optionally unloading workpieces or portions.

Overall System of the Exemplary Embodiment of FIG. 1

FIG. 1 schematically illustrates an exemplary embodiment of a system 100 for assessing the physical attributes of a workpiece, and optionally scanning, cutting, and unloading the workpieces and/or workpiece portions, in a continuous flow process. The system 100 includes a moving support surface in the form of a conveyance assembly 102 for carrying workpieces 104, which may be arranged in multiple lanes or windows, extending along the conveyance system, to be measured and optionally trimmed and/or cut into portions P. The workpieces 104 may be a food product, such as meat, poultry, or fish that are spaced along the conveyance system. Other types of workpieces may include items composed of, for example, fabric, rubber, cardboard, plastic, wood or other types of material spaced along the conveyance assembly 102.

In the following description, various alternate system embodiments are described. Alternative systems and their corresponding assemblies, apparatus and units are identified by the same part number, but with an alpha suffix. Specifically, exemplary alternative systems 100A and 100B will be described with reference to FIGS. 7 and 8. The descriptions of the parts/components of such system assemblies, apparatus and units that are the same or similar to system 100 are not repeated so as to avoid redundancy in the present application.

In the embodiment depicted in FIG. 1, the system 100 includes an optional scanning assembly having one or more scanners 110 for scanning the workpieces 104 as they enter the conveyance assembly 102. The scanners 110 gather preliminary information and data about the workpiece 104, such as its size and shape. The data and information gathered by the scanners 110 may be used to determine subsequent processing steps, if any, for the workpiece 104.

Subsequent processing steps may include measuring, cutting, trimming and/or portioning and/or harvesting. In that regard, the system 100 includes one or more processing assemblies for engaging and performing one or more processing steps on the workpiece 104. In the depicted embodiment, the system 100 includes a measurement assembly 115 for assessing physical attributes of the workpieces 104. The measurement assembly 115 is configured to measure certain desired physical attributes of the workpiece 104, such as its viscoelastic properties, temperature, etc. The system 100 further includes an optional cutting assembly 122 for cutting, trimming, and/or portioning the workpieces 104 into portions P of desired sizes or other physical parameters.

After the workpieces are scanned, measured, and cut, trimmed, and/or portioned, the workpieces 104 may be optionally unloaded from the conveyance assembly 102 by one or more unloading assemblies 132. The optional unloading assemblies 132 pick up the cut portions P from the conveyance assembly 102 and transfers the cut portions to takeaway locations, which could include optional side conveyors 140, chutes, or other locations away from the conveyance system. Alternatively, the optional unloading assemblies 132 may pick up the portioned workpieces P so that the remaining workpiece trim can be removed, and then replace the portioned workpieces onto the conveyance system at a location closely corresponding to the location from which the portioned workpieces were initially picked up by the unloading system.

The measurement assembly 115, the cutting assembly 122, and the unloading assemblies 132 are operatively associated with a powered carrier assembly 126. The powered carrier assembly 126 moves the measurement assembly 115, the cutting assembly 122, and/or the unloading assembly 132 longitudinally and laterally relative to the conveyance assembly 102 for engaging the workpiece 104 while in motion. In certain embodiments of the present disclosure, the measurement assembly 115 and the cutting assembly 122 may be carried on the same powered carrier assembly 126. In further embodiments, the optional cutting assembly 122 and the optional unloading assembly 132 may be carried on the same powered carrier assembly 126. It should be appreciated that any combination of processing assemblies may be carried on a single powered carrier assembly 126.

The conveyance assembly 102, scanners 110, measurement assembly 115, cutting assembly 122, unloading assembly 132, and carrier assembly 126 are coupled to and controlled by a processor or computer 150. As illustrated in FIG. 1, the processor/computer 150 includes an input device 152 (keyboard, mouse, touchpad, etc.) and an output device 154 (monitor, printer). The computer 150 also includes a CPU 156 and at least one memory unit 158. Rather than using a single processor or computer, one or more of the conveyor systems, scanners, measurement assemblies, cutting assemblies, unloading assemblies, and/or carrier assemblies may utilize its own processor or computer. Also, the processor/computer may be connected to a network 159 that ties system 100 to other aspects of the processing, such as downstream processing of portions P.

The general operation of the system 110 will now be described. Initially, the scanners 110 scan the workpieces 104 to produce scanning information representative of the workpieces 104, and the scanners 110 forward the scanning information to the processor/computer 150. The processor/computer 150, using a scanning program, analyzes the scanning data to determine the location of the workpieces 104 on the conveyance assembly 102. The processor/computer 150 also determines one or more workpiece regions of interest for a physical attribute measurement and develops a length, width, area, thickness, and/or volume profile of the scanned workpiece 104. The processor/computer 150 can then model the workpiece 104 to determine how it may be efficiently measured. For instance, the processor/computer 150 can run measurement software determine how to measure the time dependent strain, shape, area, weight, and/or thickness of the workpiece 104 at the one or more workpiece regions of interest. As a specific example, the known thickness of the workpiece 104 facilities efficient and rapid determination of time dependent strain or other similar measurements involving the downward movement of an actuator of the measurement assembly 115. Moreover, by computing one or more precise workpiece areas of interest for a measurement, the processing time per workpiece is very fast. Specifically, time is not wasted taking multiple preliminary measurements of the workpiece or trying to determine where a measurement should be taken.

Using the workpiece data, the processor/computer 150 functions as a controller to guide the measurement assembly 115 to a height (determined by the scanned thickness information) and a region of interest on the workpiece 104. The processor/computer 150 activates the measurement assembly 115 to take one or more measurements for assessing the physical attributes of the workpiece 104, such as its viscoelastic properties. The measurement data is processed by the processor/computer 150, which can make decisions about the best use of the workpiece or the population of workpieces.

The processor/computer 150, using the scanning program and/or an optional portioning program, may also model the workpiece 104 to determine how it should be sorted, divided, trimmed, and/or cut into end pieces P composed of specific visual and physical attributes. In that regard, the processor/computer 150 may function as a controller to control the cutter assembly 122 to portion the workpiece 104 according to selected criteria. The processor/computer 150 further controls the unloading system 132 to remove the workpiece portions P from the conveyance assembly 102 and place the portioned workpieces at one or more desired locations, either away from the conveying system, or back on the conveying system after trim has been removed.

Conveyance Assembly

Figure 2:
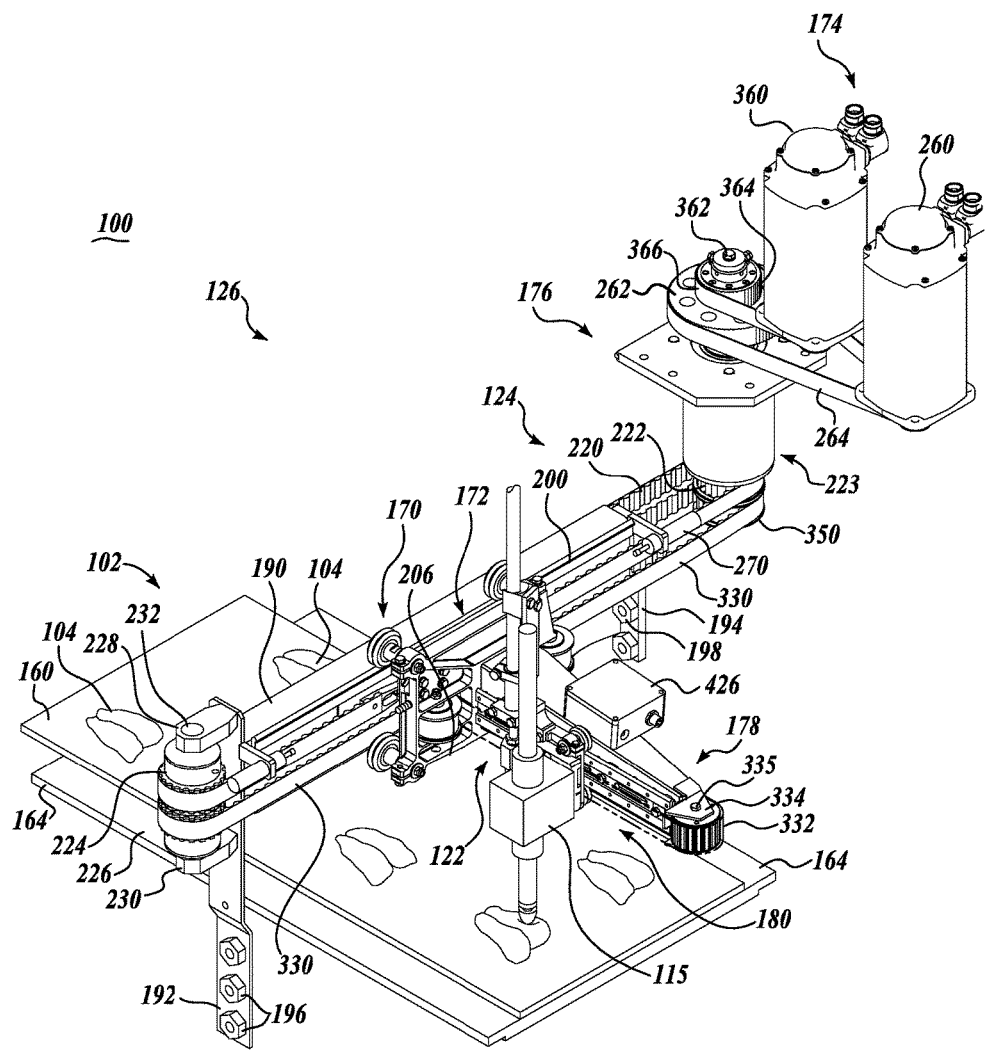
FIG. 2 is an isometric view of a carrier unit carrying a measurement assembly and a cutter assembly formed in accordance with the present disclosure.

Referring to FIGS. 1 and 2, the conveyance assembly 102 includes a moving conveyor belt 160 that is driven by drive rollers carried by a frame structure (not shown) in a standard manner. The drive rollers are in turn driven at a selected speed by a drive motor 166, also in a standard manner. The drive motor 166 can be composed of a variable speed motor to thus adjust the speed of the conveyor belt 160 as desired as the workpiece 104 is carried past scanner 110, measurement assembly 115, cutter assembly 122 and unloading assembly 132.

The moving conveyor belt 160, which is necessary flexible, does not provide sufficient underlying support and stiffness for processing the workpieces 104. More specifically, the workpieces 104 must be supported on a sufficiently stiff surface so that necessary force may be imparted onto the workpiece 104 by the measurement assembly 115. In that regard, the conveyor belt 160 slides over an underlying removable support member 164 positioned beneath the measurement assembly 115. Any suitable underlying support 164 sufficiently stiff to allow the workpieces 104 to be measured (such as by a downward force of an actuator). For instance, the underlying support 164 may be made from a suitable plastic, metal, or any other suitable material or combination of materials.

An encoder 162 is integrated into the conveyance assembly 102, for example, at drive motor 166 to generate electrical pulses at fixed distance intervals corresponding to the forward movement of the conveyor belt 160. This information is routed to processor/computer 150 so that the location(s) of the particular workpiece 104, or the portions P cut from the workpiece, can be determined and monitored as the workpiece or portions travel within system 100. This information can be used to position the measurement assembly 115, the cutting assembly 122, and/or the unloading assembly 132 relative to a workpiece 104, as well as for other purposes.

Scanning Assembly

Referring to FIG. 1, the conveyance assembly 102 carries the workpieces 104 beneath the scanners 110 of the scanning assembly. The scanners 110 may be of a variety of different types, including a video camera (not shown) to view the workpieces 104 illuminated by one or more light sources. In the case of a video camera, light from a light source (not shown) may extend across the moving conveyor belt 160 to define a sharp shadow or light stripe line or beam, with the area forwardly of the transverse beam being dark. When no workpiece 104 is being carried by the conveyor belt 160, the shadow line/light stripe forms a straight line across the conveyor belt. However, when the workpieces 104 pass across the shadow line/light stripe, the upper, irregular surface of the workpiece produces an irregular shadow line/light stripe as viewed by a video camera angled downwardly on the workpiece and the shadow line/light stripe. The video camera detects the displacement of the shadow line/light stripe from the position it would occupy if no workpiece were present on the conveyor belt 160. This displacement represents the thickness of the workpiece along the shadow line/light stripe. The length of the workpiece is determined by the distance of the belt travel (detected by encoder 162) that shadow line/light stripes are created by the workpiece.

In lieu of or in combination with a video camera, the scanning assembly may utilize an X-ray apparatus (not shown) for determining the physical characteristics of the workpiece, including its shape, mass, and weight. X-rays may be passed through the object in the direction of an X-ray detector (not shown). Such X-rays are attenuated by the workpiece in proportion to the mass thereof. The X-ray detector is capable of measuring the intensity of the X-rays received thereby, after passing through the workpiece. This information is utilized to determine the overall shape and size of the workpiece 104, as well as the mass thereof. An example of such an X-ray scanning device is disclosed in U.S. Pat. No. 5,585,603, incorporated by reference in its entirety herein.

The data and information measured/gathered by the scanners 110 are transmitted to the processor/computer 150, which records and/or notes the location of the workpieces 104 on the conveyor belt 160, as well as data pertaining to, inter alia, the lengths, widths, and thicknesses of the workpieces. With this information, the processor/computer 150, operating under the scanning system software, can develop an area profile as well as a volume profile of the workpieces. Knowing the density of the workpieces, the processor/computer 150 can also determine the weight of the workpieces or segments or sections thereof.

Although the foregoing description discusses scanning by use of a video camera and light source, as well as by use of X-rays, other three-dimensional scanning techniques may be utilized. For example, such additional techniques may be by ultrasound or moiré fringe methods. In addition, electromagnetic imaging techniques may be employed. Thus, the present invention is not limited to the use of video or X-ray methods, but encompasses other three-dimensional scanning technologies as well.

Carrier Assembly

The carrier assembly 126, which can best be seen by referring to FIGS. 1-4, is composed of a plurality of carrier units 124 spaced along the conveyance assembly 102. The carrier units 124 are adapted to carry a measurement assembly 115, optional cutter assemblies 120, and optional unloading assemblies 132, together or separately, relative to the conveyance assembly 102. For ease of illustration, only a single carrier unit 124 is labeled in detailed in FIG. 1.

Figure 3:
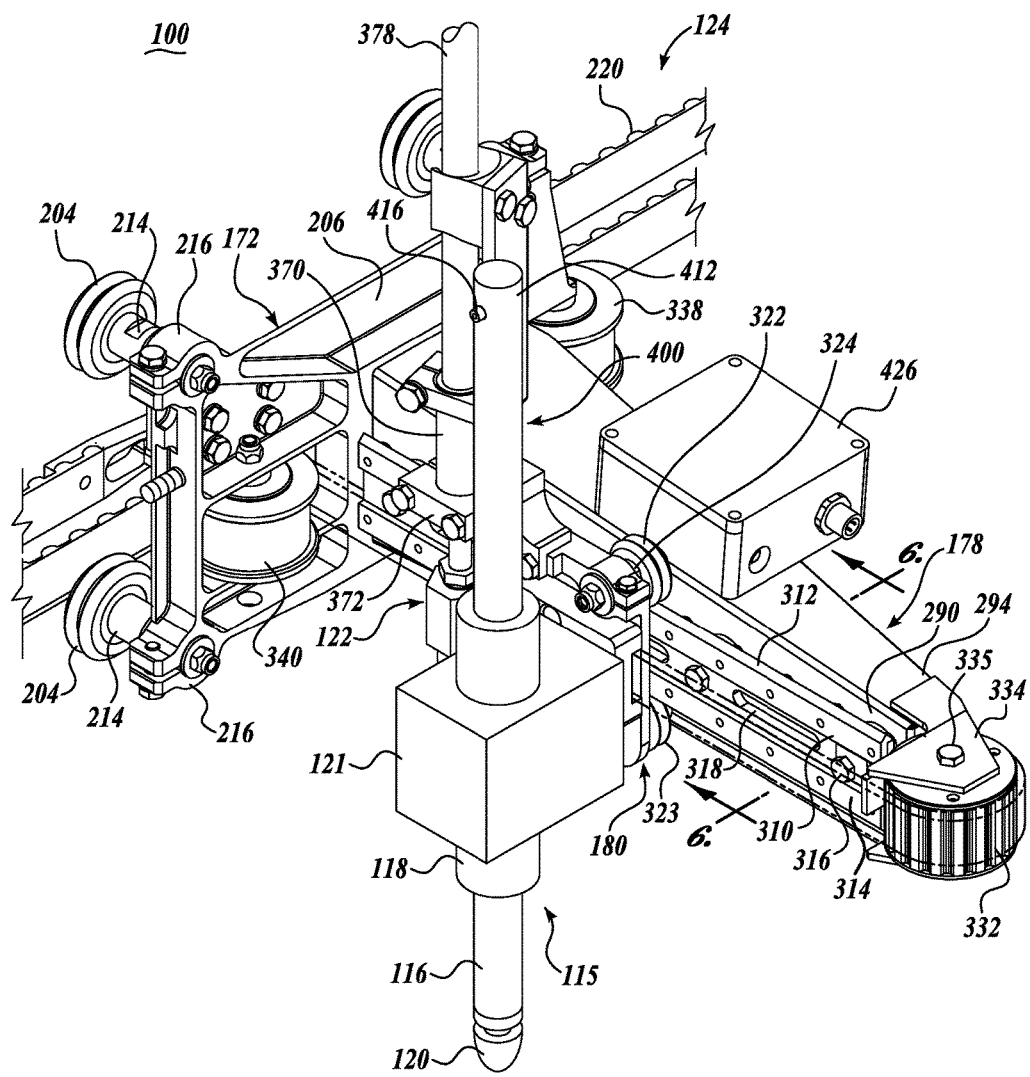
FIG. 3 is an enlarged front isometric view of the carrier unit, measurement assembly and cutter assembly FIG. 2.
Figure 4:
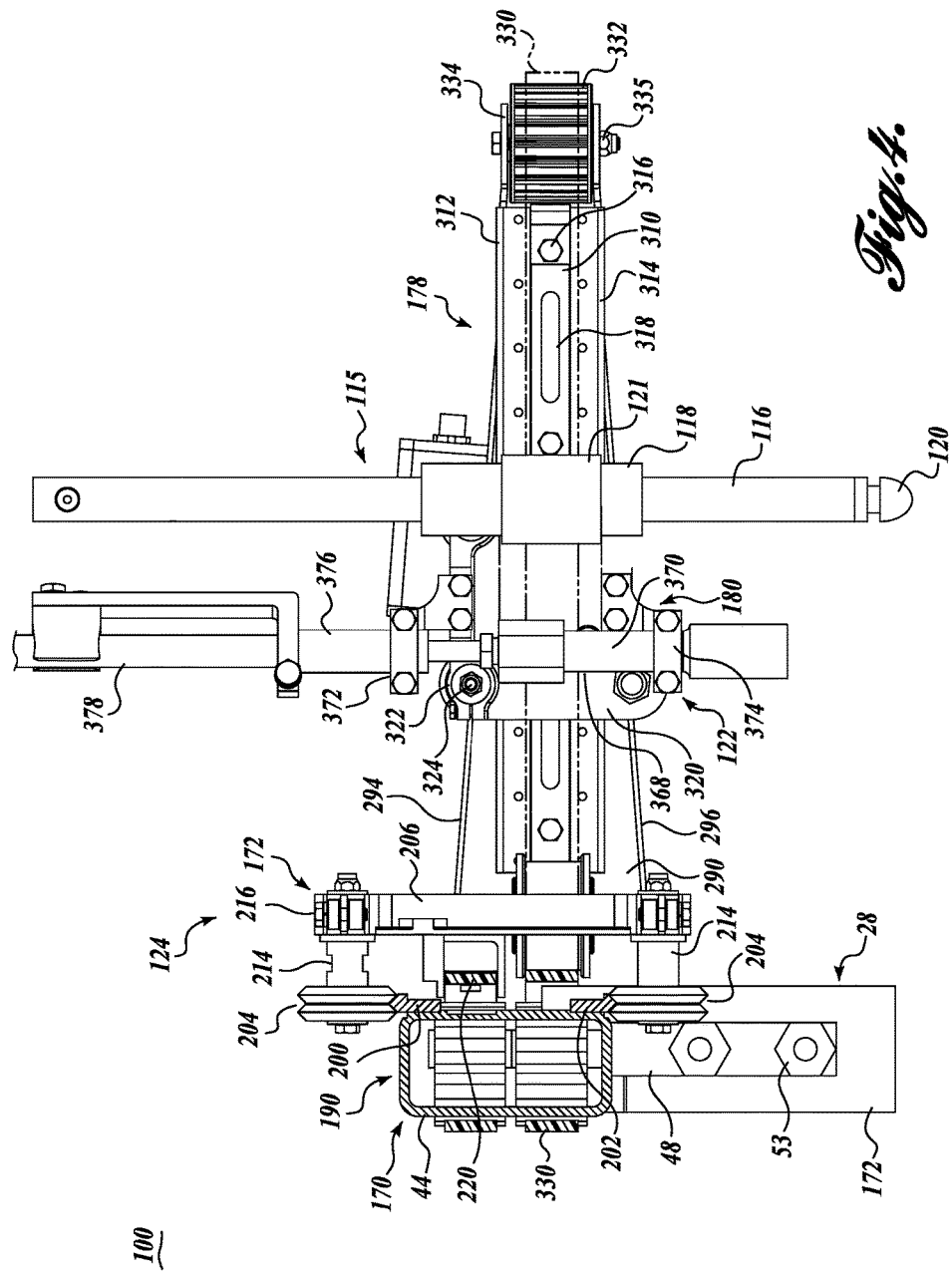
FIG. 4 is a front side view of the carrier unit, measurement assembly, and cutter assembly of FIG. 3.

As can be seen in more detail in FIGS. 2-4, each carrier unit 124 includes a transverse support structure or gantry 170 extending across the conveyance assembly 102 for supporting and guiding a transverse carriage 172 along the gantry 170 transversely to the direction of movement of the conveyor belt 160. The transverse carriage 172 is powered by a drive system including, in part, a motive system 174 and a drive train 176. A longitudinal support structure 178 is cantilevered outwardly from the transverse carriage 172 in a direction generally aligned with the direction of movement of the conveyor belt 160. A longitudinal carriage 180 is adapted to move along the longitudinal support structure 178 by a drive system which in part includes the motive system 174.

The longitudinal carriage 180 is configured to carry a measurement assembly 115, a cutting assembly 122, and/or an unloading assembly 132 along the longitudinal support structure 178 in the direction of the movement of the conveyor belt 160. At the same time, the longitudinal support structure 178, mounted to the transverse carriage 172, may move along the gantry 170 transversely to the direction of movement of the conveyor belt 160. As such, the carrier unit 124 is configured to move the measurement assembly 115, the cutting assembly 122, and/or the unloading assembly 132 (and any combination thereof) to a desired X-Y location of the conveyor belt 160 for processing a desired workpiece 104.

The components of the carrier unit 124 will now be described in further detail. The gantry 170 is composed of a transverse support structure 190 that spans transversely across the conveyor belt 160 at an elevation spaced above the conveyor belt 160. The transverse support structure 190 can be composed of a hollow, rectangular construction, but may be formed in other manners and shapes without departing from the spirit or scope of the present invention. A track is defined along the transverse support structure 190 for guiding transverse carriage transversely across the conveyor belt 160. The track is composed of an upper rail 200 and a lower rail 202. The upper and lower rails 200 and 202 are secured to a side face of the transverse support structure 190, with the upper rail 200 extending along an upper corner of the transverse support structure 190 and the lower rail 202 extending along a lower corner of the transverse support structure 190. As also illustrated, the upper surface of the upper rail 200 and the lower surface of the lower rail 202 are crowned to engage with concave outer perimeters of rollers 204 of transverse carriage 172. As such, the transverse carriage 172 is held captive on the track while traveling back and forth along the transverse support structure 190.

The ends of transverse support structure 190 are supported by at least one elongated upright bracket 192 to position the transverse support structure 190 a selected distance above the conveyance assembly 102. As shown in FIG. 2, bracket 192 is fixed to the adjacent ends of the transverse support structure 190 and extend downwardly therefrom. A plurality of hardware members 196, such as fasteners, extend through clearance holes (not shown) formed in a lower, offset portion of bracket 192 for attachment to the conveyance assembly 102 or to a frame structure for the conveyance assembly 102. Bracket 194 extends downwardly from the opposite end of the transverse support structure 190. In this regard, hardware members 198, such as fasteners, extend through clearance holes provided in the lower end of bracket 194 for attachment to the conveyance assembly 102 or frame. In this manner, the transverse support structure 190 is securely mounted a selected distance above the conveyance assembly 102 or the frame thereof.

As can best be seen by referring to FIGS. 3 and 4, transverse carriage 172 includes a substantially planar, generally rectangularly shaped bed portion 206 having a reinforced outer perimeter for enhanced structure integrity. The carriage rollers 204 are attached to corners of the bed 206 by stub axles 214, which engage within through-bores formed in bosses 216 that extend transversely from each of the four corners of the carriage bed 206. Antifriction bearings (not shown) are utilized between the rollers 204 and the stub axles 214 to enhance the free rolling of transverse carriage 172 along transverse support structure 190.

Transverse carriage 172 is powered to move back and forth along transverse support structure 190 by motive system 174. In this regard, a timing belt 220 extends around a driven pulley 222 located at the lower end of drive shaft assembly 223 of motive system 174 and also around an idler pulley 224 of an idler assembly 226 mounted on the upper end of bracket 192 by upper and lower bracket ears 228 and 230. As such, the belt 220 makes a loop around the transverse support structure 190, extending closely along the sidewalls of the structure. The idler pulley 224 is adapted to rotate freely about central shaft 232 of the idler assembly 226 through the use of an antifriction bearing (not shown), with the upper and lower ends of the shaft being retained by bracket ears 228 and 230.

Figure 5:
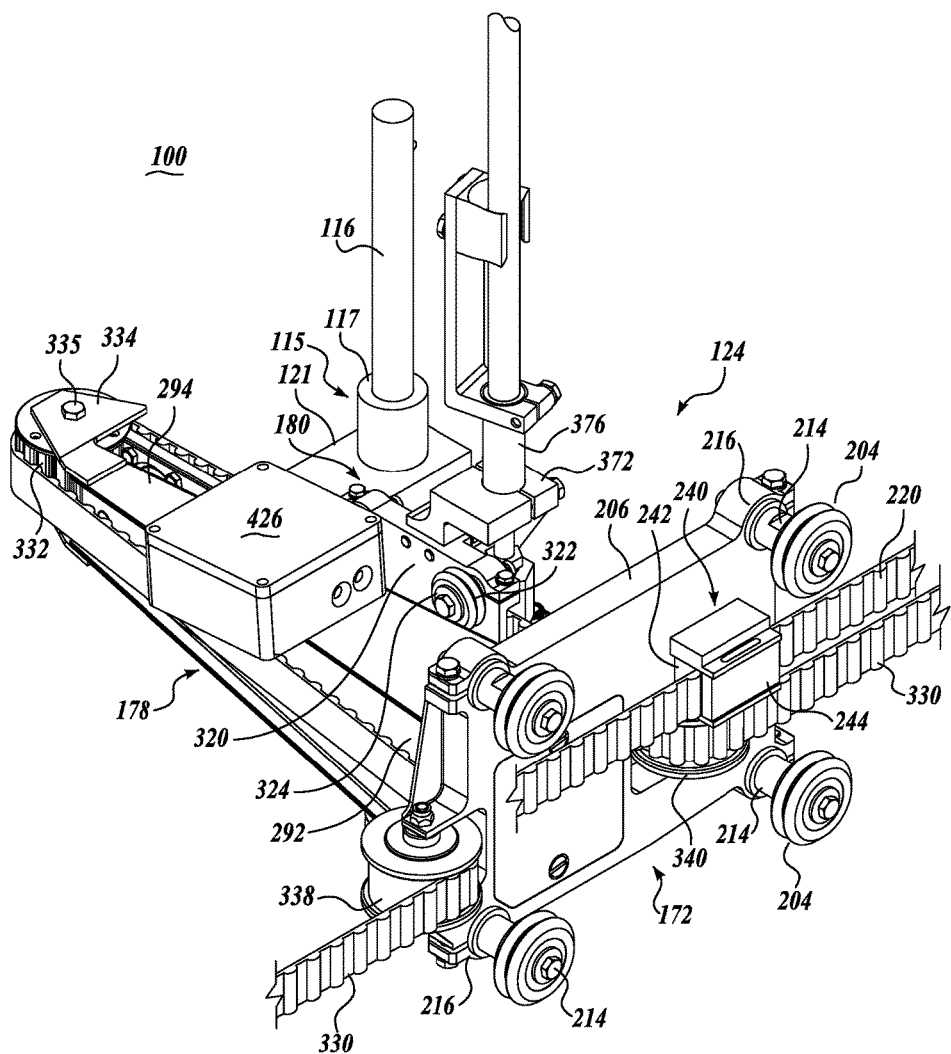
FIG. 5 is a rear isometric view of the carrier unit, measurement assembly, and cutter assembly of FIG. 3.

The belt 220 is connected to the backside of the carriage bed 206. As most clearly shown in FIG. 5, a spring-loaded clamping structure 240 connects the belt 220 to the carriage bed 206. In this manner, if the carriage bed 206 becomes jammed or locked along the transverse support structure 190, if the carriage bed 206 is ever in a "runaway" condition, or if motive system 174 malfunctions tending to cause the carriage bed 206 to overrun transverse support structure 190, the belt 220 can slide or move relative to the carriage bed 206. As such, potential damage to any processing assemblies (i.e., measurement assembly 115, cutting assembly 122, and/or unloader assembly 132) may be avoided or at least minimized.

The clamping structure 240 includes a base or back block 242 mounted to the back face of the carriage bed 206. A face plate 244, mounted to the back block 242, is resiliently clamped against a toothed surface of belt 220. The surface of face plate 224 that interfaces with the belt 220 is ridged to match the contours of the belt 220. Normally the clamping force that clamps the face plate 244 to the block 242 securely clamps the belt 220 to the clamping structure. However, if the tension in the belt 220 exceeds a certain level, then the belt 220 is able to slip relative to the clamping structure.

Referring to FIG. 2, the motive system 174 includes a programmable servo motor 260 configured to control the movement of the transverse carriage 172 back and forth along transverse support structure 190 as desired. The servo motor 260 is positioned at a location substantially insulated from moisture or other contaminants that may be associated with the work/processing being carried out on the workpieces 104. A hollow drive shaft (not shown) extends down through drive shaft assembly 223. The driven pulley 222 is attached to the lower end of the hollow drive shaft and a drive pulley 262 is attached to the upper end of the hollow drive shaft. The drive pulley 262 is connected by belt 264 to an output drive pulley (not visible) powered by servo motor 260. It will be appreciated that by the foregoing construction, the servo motor 260 is located remotely from the transverse carriage 172, with the driving force applied to the transverse carriage 172 by the lightweight timing belt 220.

By the foregoing construction, motive system 174 is capable of quickly accelerating and decelerating transverse carriage 172 for movement along transverse support structure 190. Although ideally motive system 174 utilizes a servo motor, other types of electrical, hydraulic, or air motors may be employed without departing from the spirit or scope of the present invention. Such motors are standard articles of commerce.

Next, referring specifically to FIGS. 2-5, the longitudinal support structure or beam 178 cantilevers transversely from transverse carriage 172 to be carried by the carriage. The beam 178 is composed of a vertical sidewall 290 which extends substantially perpendicular from the carriage bed 206. The opposite sidewall 292, rather than being substantially perpendicular to the carriage bed 206, tapers towards sidewall 290 in the direction away from the carriage bed 206. Likewise, the top and bottom walls 294 and 296 of beam 178 taper towards the free end of the beam, thereby to cooperatively form a generally tapered beam shape. As will be appreciated, this enhances the structural integrity of the beam 178 while reducing its weight relative to a parallelpiped structure.

Figure 6:
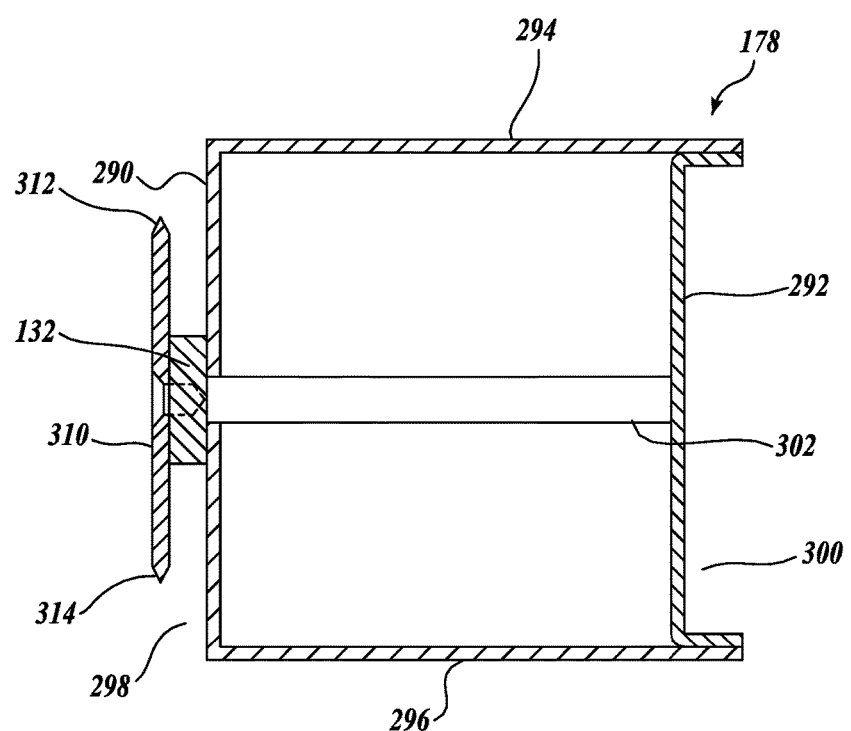
FIG. 6 is a cross-sectional view of a portion of the carrier unit shown in FIG. 3, taken substantially across line 6-6.

As illustrated in FIG. 6, in one form the beam 178 may be of hollow construction, composed of two channel-shaped members 298 and 300. Channel member 300 is shallower than channel member 298 and nests within channel-shaped member 298 so that the flanges of channel member 300 overlap the free end edges of the flanges of channel-shaped member 298. A plurality of spacers 302 are disposed within the beam member 178 and located along its length to bear against the sidewalls 290 and 292 of the channel members 298 and 300. The flanges of the two channel members are attached together and the spacers 302 are attached to the channel members by any convenient means, including by weldments. It will be appreciated that by the foregoing construction, beam 178 is not only lightweight, but also of sufficient structural integrity to carry significant weight without deflection. Lastly, beam 178 may be secured to the carriage bed 206 by any appropriate technique, including by hardware fasteners, weldments, etc.

Referring to FIGS. 2 and 3, an elongate track 310 for longitudinal carriage 180 is mounted on and extends longitudinally on beam sidewall 290. Track 310 includes upper and lower edge portions 312 and 314 that are spaced away from sidewall 290 to define upper and lower rails for guiding the longitudinal carriage 180. The track 310 is attached to beam sidewall 290 by a plurality of hardware members 316 that extend through clearance holes formed in the track 310. Spacers (not shown) may be disposed between sidewall 290 and the track 310 to space the track 310 away from the sidewall 290. Also to minimize the weight of track 310, spaced apart, cut-out oval openings 318 may be formed between the upper and lower edge portions 312 and 314.

The longitudinal carriage 180 includes a substantially planar, rectangularly shaped bed portion 320 (see FIG. 4) that is adapted to travel along track 310. In this regard, a pair of upper rollers 322 and a pair of comparable lower rollers 323 are secured to the bed portion 320. The rollers 322 and 323 have concave outer perimeter portions sized to closely engage with the correspondingly crowned upper and lower edge portions 312 and 314. The upper and lower rollers 322 and 323 are mounted on stub shafts 324 extending transversely from the bed portion 320. Ideally, but not shown, anti-friction bearings are utilized between the stub shafts 324 and the rollers to enhance the free movement of the longitudinal carriage 180 along track 310.

Longitudinal carriage 180 is moved back and forth along track 310 by the motive system 174 that powers a timing belt 330. To this end, an idler pulley 332 is mounted on the free end of support beam structure 178 by a formed bracket 334 which is fixedly attached to the beam structure 178. A pivot shaft 335 extends through the center of an antifriction bearing mounted within pulley 332, with the ends of the shaft retained by the upper and lower ears of bracket 334.

The ends of belt 330 are attached to the bed 320 of longitudinal carriage 180. This attachment can be carried out in a number of ways, including the use of a system that is similar to that described above regarding the attachment of belt 220 to transverse carriage 172. Also, the belt 330 extends partially around directional pulleys 338 and 340, anti-frictionally mounted on carriage bed 206 to direct the belt along transverse support structure 190 and along longitudinal support structure 178.

Rotation of a drive pulley 350 positioned on the end of the drive shaft assembly 223 results in movement of the belt 330, which in turn causes the longitudinal carriage 180 to move along track 310. In this regard, the motive system 174 includes a servo motor 360 which is drivingly connected with drive pulley 350 by a drive shaft 362 that extends downwardly through drive shaft assembly 223. A driven pulley 364 is attached to the upper end of drive shaft 362, which is connected via timing belt 366 to a drive pulley (not visible) powered by motor 360. The drive shaft 362 is disposed within the hollow drive shaft extending between pulleys 222 and 262.

As with motor 260, other types of well-known and commercially available rotational actuators may be utilized in place of servo motor 360. Also, as noted above, motive system 170 is located remotely from not only transverse carriage 172, but also longitudinal carriage 180. As a result, the mass of the motive system 174 is not carried by either of the two carriages. Rather the motive system is positioned at a stationary location, with the drive force being transferred from motive system 174 to longitudinal carriage 180 by a lightweight timing belt 330. As a consequence, the total mass of the moving portions of carrier assembly 126 (transverse carriage 172, support beam 178 and longitudinal carriage 180) is kept to a minimum. This allows extremely high speed movement of the two carriages, with accelerations exceeding eight gravities.

Figure 7:
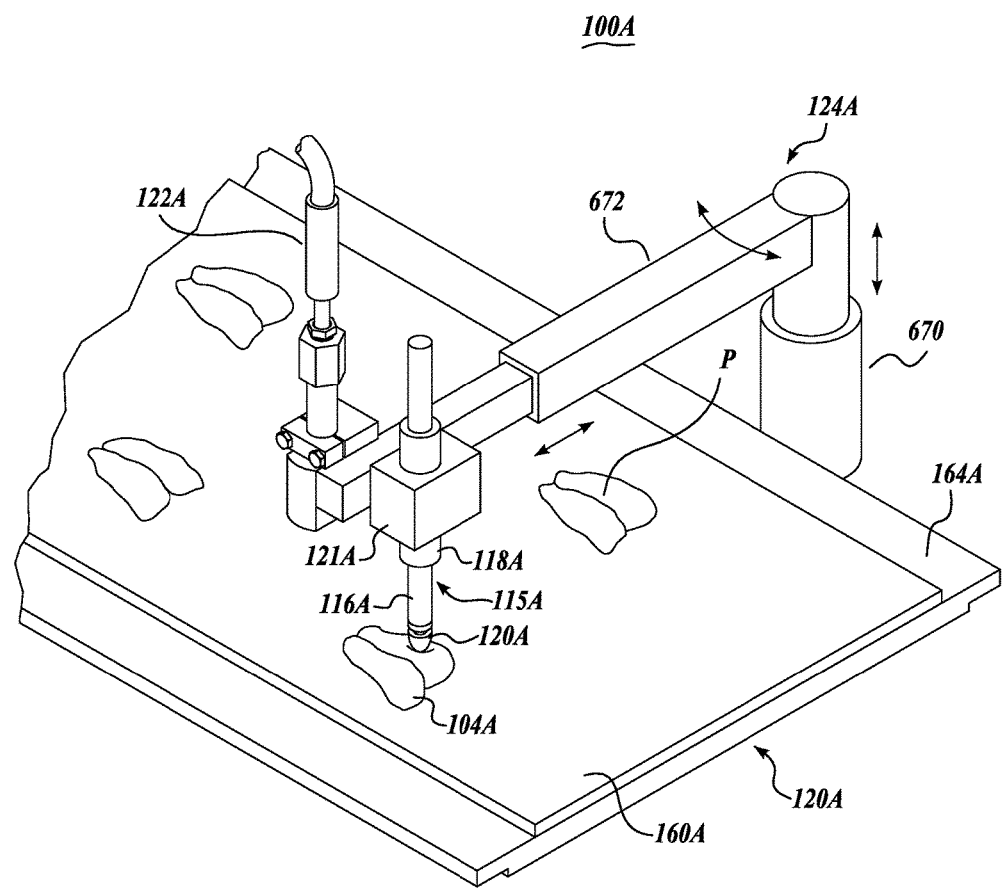
FIG. 7 is an isometric view of a first alternative embodiment of a carrier unit carrying a measurement assembly and a cutter assembly.

Referring to FIG. 7, a first alternative embodiment of a carrier unit 124A for use in a system 100A is depicted. The carrier unit 124A is configured to rotate, elevate, and extend to appropriately position the measurement assembly 115A and/or the cutting assembly 122A above the conveyor belt 160A. The carrier unit 124A includes a rotatable and elevatable post assembly 670 mounted along the side of the conveyance assembly 102A. The post assembly 670 is powered to raise and lower relative to the surface of the conveyor belt 160A. The post assembly 670 is also powered to rotate and extend a telescoping beam 672 over the conveyor belt 160. The beam 672 is powered to extend and retract along its length so as to position a measurement assembly 115A and a cutting assembly 122A at desired locations over the surface of the conveyor belt 60. The cutting assembly 122A is mounted to one side of the free end of the beam 672 and the measurement assembly 115A is mounted to the opposite side of the free end of the beam. It will be appreciated that the cutting assembly 122A and measurement assembly 115A are structurally and operationally similar or identical to the corresponding cutting assembly 122 and measurement assembly 115 described above.

Figure 8:
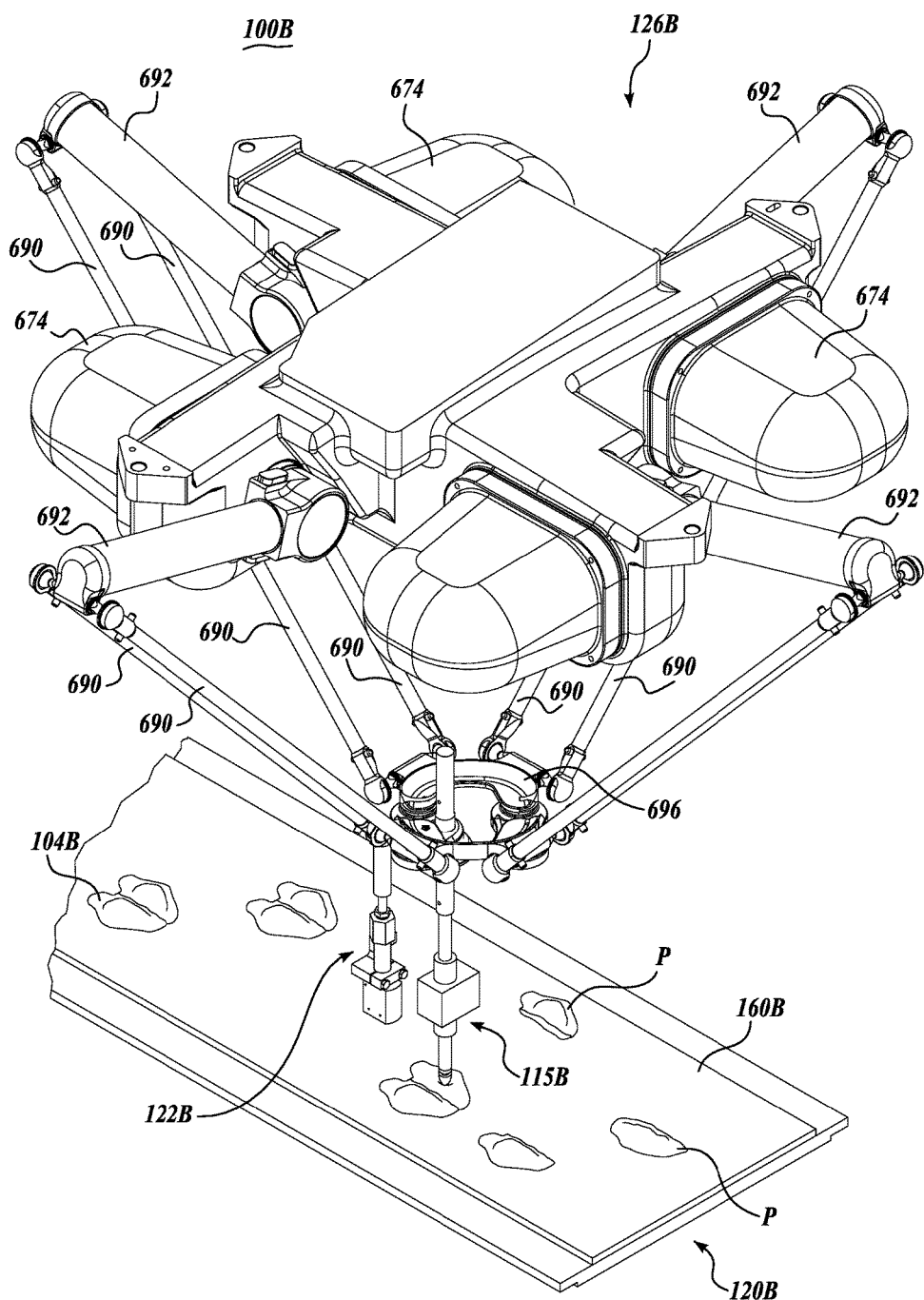
FIG. 8 is an isometric view of a second alternative embodiment of a carrier unit carrying a measurement assembly and a cutter assembly.

Referring to FIG. 8, a second alternative embodiment of a carrier unit 124B for use in a system 100B is depicted. The carrier unit 124B is a robotic structure composed of four sets of powered arm pairs 690 that are connected to each other at one end (upper end) to a powered pivot arm 692, which in turn is connected to a rotary actuator 694 that is powered to rotate about a horizontal axis. Each of the four pivot arms 692 extend outwardly from a central axis in a quadrant arrangement. The lower or opposite ends of the arm pairs 690 are connected to a carrier head or ring 696 to which a cutting assembly 122B and a measurement assembly 115B are mounted.

The carrier unit 124B is capable of moving the carrier head 696, and thus the cutting assembly 122B and measurement assembly 115B in any direction over the conveyor 160, including side to side, longitudinally, up and down, as well as diagonally. The carrier unit 124B is also capable of lifting the cutting assembly 122B and measurement assembly 115B away from vertical into a desired orientation.

It will be appreciated that, by the foregoing construction, the same type of carrier may be used to carry one or more measurement assemblies 115, cutter assemblies 122, and/or unloading assemblies 132, thereby resulting in commonality of components of the system 100 and an efficiency of spare parts required for the carrier units 124. However, the longitudinal carriage 180 can be configured so that rather than mounting a measurement assembly 115 and a cutting assembly 122 (or a cutting assembly 122 and an unloading assembly 132), as shown in FIG. 1, two or more measurement assemblies 115, two or more cutter assemblies 122, and/or two or more unloading assemblies 132 can be mounted on the longitudinal carriage 180 of a carrier unit 124. In that regard, any combination of measurement assemblies 115, cutter assemblies 122, and/or unloading assemblies 132 may be mounted to the longitudinal carriage 180 of a carrier unit 124. This may be carried out, for example, by forming the applicable hole patterns on the carriage bed 320 for corresponding hardware members.

It should be appreciated that any suitable carrier system 126 may be used without departing from the scope of the present disclosure. For example, while various carrier units 124, 124A, and 124B have been described above, other carrier units may be utilized. For example, a carrier unit may be composed of other types of robotic apparatus described above. Furthermore, sweeping systems for moving or sweeping trim and/or nuggets and/or portioned pieces, such as those described in U.S. Patent Application Publication No. 20150205288, entitled "System for Cutting and Unloading Portions," filed on Jan. 22, 2014, the disclosure of which is incorporated by reference herein in its entirety, may be utilized in conjunction with any of the carrier units.

Cutting Assembly

As illustrated in FIGS. 1-5, a cutting assembly 122 may be secured to a longitudinal carriage 180 for portioning, cutting, and/or trimming the workpieces 104 as they move along the conveyor belt 160. The cutting assembly 122 may be mounted on the same or different carriage than the measurement assembly 115 (as shown in FIGS. 2-5) and/or the unloading assembly 132, or even on a different type of actuator/carriage.

Although any suitable cutting assembly 122 may be used, in the depicted embodiment, the cutting assembly 122 is embodied as a high pressure liquid nozzle assembly 368. The nozzle assembly emits a very focused stream of high pressure water disposed in a downward cutting line that is nominally transverse to the plane of conveyor belt 160. The nozzle assembly 368 includes a body portion 370 that is secured to the carriage bed 320 by a pair of vertically spaced apart brackets 372 and 374. The nozzle assembly 368 includes a lower outlet directed downwardly toward conveyor belt 160. A fitting 376 is attached to the upper end of nozzle body 370 for connecting the nozzle body 370 to a high pressure fluid inlet line 378. High pressure liquid nozzles of the type embodied by work tool 122 are well-known articles of commerce.

Unloading Assembly

As illustrated in FIG. 1, an unloading assembly 132 may be secured to a longitudinal carriage 180 for unloading whole or portioned/trimmed/cut workpieces 104 as they move along the conveyor belt 160. The unloading apparatus may be mounted on the same or different carriage than the cutting assembly 122 and/or the measurement assembly 115, or even on a different type of actuator/carriage. Any suitable unloading assembly may be used, such as one of the unloading assemblies illustrated and described in U.S. Patent Application Publication No. 20150205288, entitled "System for Cutting and Unloading Portions", filed on Jan. 22, 2014, the disclosure of which is incorporated by reference herein in its entirety. Accordingly, a detailed description of the unloading assembly 132 will not hereinafter be provided.

Referring specifically to FIG. 1, the whole or portioned workpieces 104 when lifted off the conveyor belt 160 by unloading apparatus 132 may be placed on a takeaway conveyor 140 extending along the side of conveyance assembly 102. From conveyor 140, the portion pieces P may proceed for further processing.

The conveyor 140 may be divided into first and second conveyance lines 140A and 140B, with each line providing a dedicated space for transporting selected workpieces 104 to first and second locations. For instance, portioned workpieces P' having acceptable viscoelastic properties (according to predetermined criteria) may be transported to a first location for a first type of subsequent processing (breading, cooking, packaging, etc.). Portioned workpieces P" having unacceptable viscoelastic properties (according to predetermined criteria) may be transported to a second location for a second type of subsequent processing (discarding, grinding, tenderizing, etc.).

Alternatively or in addition thereto, the portioned pieces may be placed within dedicated chutes (not shown) positioned along the side of the conveyor belt 160, from which the portioned pieces P, P', and/or P" may drop down into a conveyor or bin (not shown) for further processing. Moreover, rather than using a single side conveyor 140, one or more side conveyors similar to conveyor 140 can be vertically stacked or positioned on both sides of the main conveyance assembly 102. In this manner, different portioned pieces P, P', and/or P" can be placed on different conveyors based on various criteria (such as the viscoelastic properties, size, thickness, weight of the portioned pieces, or other characteristics) for transport to different types of subsequent processing.

Measurement Assembly

As illustrated in FIGS. 1-5, a measurement assembly 115 may be secured to a longitudinal carriage 180 for measuring physical properties of the workpieces 104 as the workpieces 104 move along the conveyor belt 160. In other words, the measurement assembly 115, carried by the carrier unit 124, is capable of measuring physical properties of the workpieces 104 while the workpieces are in motion, thereby matching the motion of the workpieces. The measurement assembly 115 is moved by the carrier unit 124 in close proximity to the workpiece region of interest (i.e., the x-, y-, and z-location determined by the size, shape, volume, etc. of the workpiece 104 when scanned by the scanner 110). The measurement assembly 115 may be mounted on the same or different carriage than the cutting assembly 122 (as shown in FIGS. 2-5) and/or the unloading assembly 132, or even on a different type of actuator/carriage.

In one exemplary embodiment, the measurement assembly 115 is configured to measure the viscoelastic properties (i.e., tenderness, resilience, stiffness, texture, etc., collectively referred to as "viscoelastic properties") of the workpiece 104 for assessing the workpiece quality (e.g., woody chicken v. non-woody chicken). In at least one specific embodiment, the measurement assembly 115 measures the force response of the workpiece during deformation as a function of time, or the time dependent strain.

Although the measurement assembly 115 may measure the time dependent strain or other viscoelastic properties in any suitable manner, in the depicted embodiment, the measurement assembly 115 is configured to deform the workpiece 104 at a known rate in a controlled downward and upward motion over the workpiece region of interest. When engaging and deforming the workpiece, the measurement assembly 115 simultaneously measures the force response of the workpiece using a suitable measurement device, such as a strain gauge.

The deformation of the workpiece 104 can occur at a constant speed, at a frequency of interest, or at a changing rate of speed, or any combination thereof for a predetermined distance. In one example, the measurement assembly 115 is moved downwardly at a constant velocity for a predetermined distance, where the predetermined distance is proportional to the thickness of the workpiece. Specifically, for a 35 mm thick workpiece, the predetermined distance would be about 7 mm or 7/35=20% compression. For a 12 mm thick workpiece, the predetermined distance would be about 2.4 mm or 2.4/12=20% compression.

It should be appreciated that the measurement assembly 115 may instead be configured to measure other or additional physical properties of the workpiece, such as the workpiece temperature, to assess workpiece quality and/or to determine subsequent processing steps for the workpiece. Moreover, multiple physical measurements may be taken per work piece.

The measurement assembly 115 includes wired or wireless means for communicating with the computer 150. As such, the computer 150 may control the measurement assembly 115, and the measurement assembly 115 may send the measurement data to the computer 150. The measurement data is processed by the computer 150, which can make decisions about the best use of the workpiece or the population of workpieces. In particular, the computer 150 records the force response of the workpiece, calculates one or more commercially important physical parameters for the identified workpiece at the region of interest, records a result for the workpiece, and optionally makes decisions about the best use of the workpiece or the population of workpieces based upon the measured value or values.

The measurement assembly 115 has a sufficiently fast cycle time such that 100% of the workpieces may be tested in the continuous flow of the system 100. As such, no down time is required to test the workpieces, and quality control is increased. Moreover, the measurement assembly 115 is configured to test the viscoelastic properties of the workpiece without damaging the workpiece. As such, tested workpieces that meet the test criteria are not wasted.

Referring to FIGS. 2-4, an exemplary embodiment of a measurement assembly 115 configured to measure viscoelastic properties of a workpiece as time dependent strain is depicted. In general, the measurement assembly 115 is embodied as a linear actuator that is configured to reciprocate a measurement device between an upward and downward position for deforming and measuring the deformation in the workpiece.

More specifically, the measurement assembly 115 is embodied as a linear actuator or linear servo motor, such as the stainless steel linear motor available from LinMot USA, Inc. The linear servo motor includes a shaft 116 movable precisely within a casing 118 up and down, moving away from and toward conveyor belt 160. The shaft 116 delivers an impact to the workpiece that is sufficient to deform the workpiece, but not damage the workpiece. Moreover, the linear servo motor preferably has a cycle time of about 1 second or less, which is a 60 fold reduction in cycle time compared to prior art lab tests.

An end effector 120 is defined on the distal end of the shaft 116 that is engageable with a workpiece 104. The effector 120 may be a suitable configuration, such as a round nose, such that it engages and deforms, but does not destroy the workpiece. The end effector 120 is also configured to deliver the impact load in the workpiece to a measurement device.

A suitable measurement device (not shown), such as a waterproof, precision, fast response strain gauge, is integrated within the end effector 120 and/or the shaft 116 for simultaneously measuring the force response of the workpiece when the end effector 120 engages and deforms the workpiece 104. In that regard, the conveyor belt 160 is supported underneath by a stiff structural member, such as granite, metal, etc., to substantially eliminate all vibrations and other noise that may affect the force measurement. The measurement device may also include an energy sensor, such as a temperature sensor to detect the temperature of the workpiece when the end effector 120 engages the workpiece 104. The temperature or other energy reading may be processed by the computer 150 and taken into account in assessing the viscoelastic properties of the workpiece 104. For instance, a chicken breast at a low temperature below the latent zone may be very stiff and firm (greater than 0% ice crystals), but the chicken breast may not otherwise qualify as "woody chicken."

The measurement assembly 115 is secured to the longitudinal carriage 180 through a suitable mounting member 121. It should be appreciated that the measurement assembly 115 may instead be secured to the longitudinal carriage 180 through any suitable bracket assembly or other mounting assembly. With the measurement assembly 115 mounted on the longitudinal carriage 180, the shaft 116 is oriented vertically and nominally transverse to the plane of conveyor belt 160, allowing the end effector 120 to forcibly engage the workpiece 104 in a downward direction. As described above, the longitudinal carriage 180 is moved to a selected X-Y location by the carrier unit 124 (as controlled by the computer 150) to take a measurement of the workpiece at an area of interest.

It should be appreciated that other measurement assembly configurations may instead be used to measure the viscoelastic properties of a workpiece, or other desired properties. For instance, other means of linear actuation include but are not limited to pneumatic cylinders or rack and pinion actuators. Another alternative embodiment of the measurement assembly may employ force feedback systems within the linear servo motor in lieu of a separate force gauge mounted on the actuator shaft or in other proximity. Another alternative embodiment of the measurement assembly may employ a sending and receiving unit mounted in the end effector similar to that used in water depth sensing instruments in the marine industry. In such an alternative embodiment, the force response could be measured in the supporting structure rather than in the end effector. As yet another alternative embodiment, the measurement assembly 115 could be combined with visual scan information such as x-ray diffraction, scatter, or luminescence to improve accuracy and discrimination between workpieces. As yet another alternative, the linear servo motor of the measurement assembly could be programmed to vibrate when it reached a targeted compression level of the workpiece. In such an embodiment, the strain gauge could detect the response of the workpiece to a vibration or impulse. The calibrated slide hammer experiment below shows that it may be possible to discriminate between workpieces based upon the dampening rate of the material. Thus, it should be appreciated that the descriptions and illustrations provided herein are exemplary only, and are not intended to limit the scope of the present disclosure.

Experiment

An experiment was conducted by the inventors to test the viscoelastic properties of a first, soft viscoelastic workpiece and a second, stiff or hard viscoelastic workpiece on a lab bench. The first and second workpieces mimic the viscoelastic properties of a normal chicken breast and a woody chicken breast, respectively. Such an experiment was conducted to determine the expected response signal for a normal chicken breast and a woody chicken breast to help identify criteria for determining if a chicken breast piece qualifies as "woody chicken." The criteria described below and illustrated in FIGS. 10A-10C could be implemented into the systems 100, 100A, and/or 100B described above, as well as systems 500, 500A, and 500B described below to test and process chicken breasts or any suitable viscoelastic workpiece. In particular, the measurement data sent to the computer of the scanning and control assembly may be compared against the experiment criteria, or similar criteria, for assessing the quality of the workpiece and how the workpiece or the population of workpieces should be used.

Figure 9:
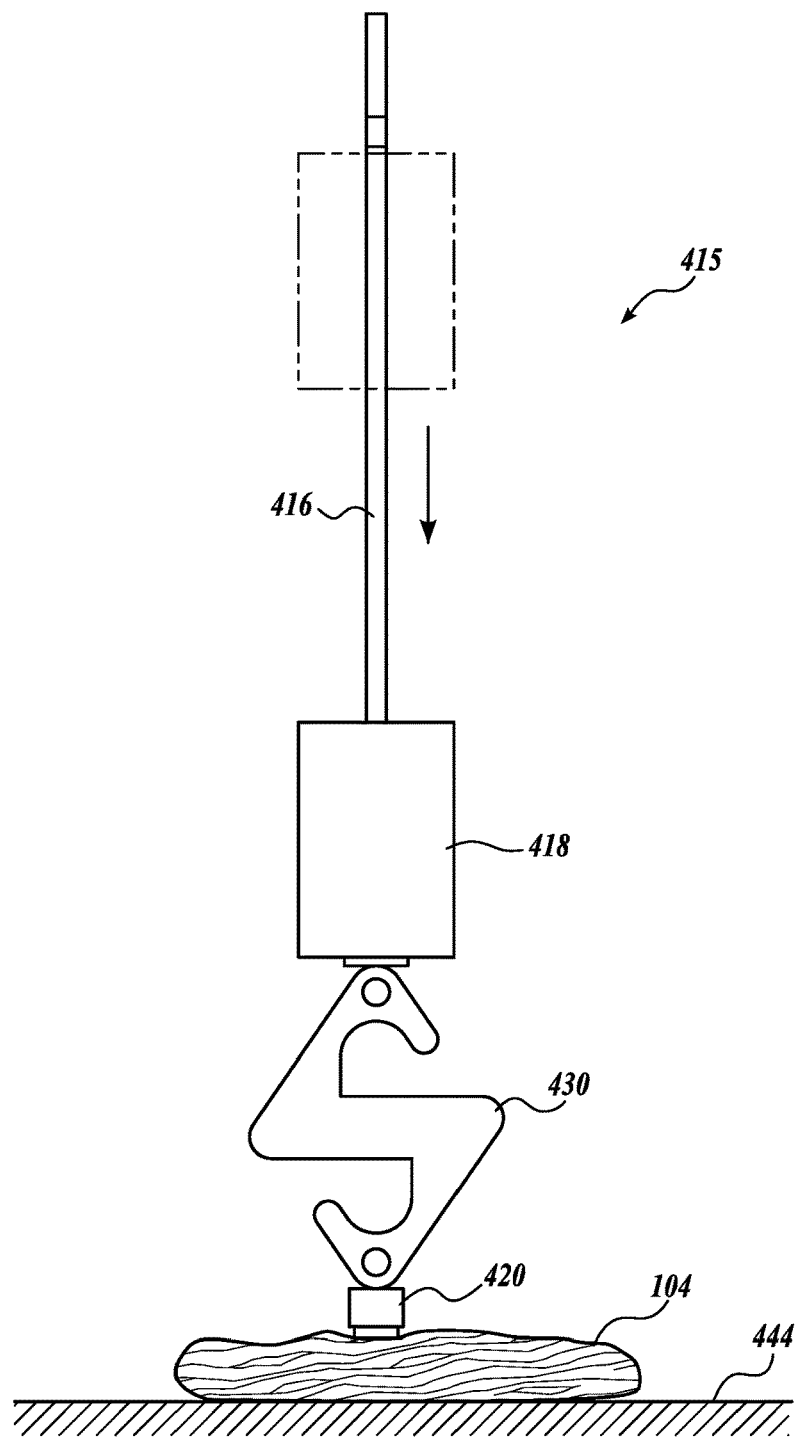
FIG. 9 is a side view of a measurement assembly used in an experiment for determining viscoelastic property criteria of a workpiece.

Referring to FIG. 9, the measurement assembly 415 used for the experiment included a calibrated slide hammer 418 slidable on a slide rod 416 between a first position (shown in phantom lines) and a second position engaging a strain gauge 430. An end effector 420 on the bottom end of the strain gauge 430 delivered the impact force of the slide hammer 418 and deformed the workpiece 104. The workpiece 104 rested on a stiff member 444 that was composed of granite. The strain gauge 430 measured the response (Force (Newtons) v. Time (seconds)) on the workpiece 104 with the strain gauge 430 to determine the strain response in the workpiece 104.

Three different tests were performed, each test including the measurement of a first, soft viscoelastic workpiece (similar to a "normal" chicken breast) and a second, stiff or hard viscoelastic workpiece (similar to a "woody" chicken breast). The test results are illustrated in the response curves of FIGS. 10A-10C, which depict the damping ratio of each workpiece (how oscillations in the workpiece decay after the impact). As can be seen in the figures, the damping ratio of the first, soft viscoelastic workpiece (similar to a "normal" chicken breast) in each test is visually similar, and the damping ratio of a second, stiff or hard viscoelastic workpiece (similar to a "woody" chicken breast) in each test is visually similar. Accordingly, data could be extrapolated from the response curves to identify criteria for assessing whether a viscoelastic workpiece is soft or hard (e.g., whether a chicken breast is "normal" or "woody.")

Figure 10A:
FIGS. 10A-10C are graphical results of time dependent strain (Force (Newtons) versus Time (Seconds)) in first and second tested workpieces of the experiment.
Figure 10B:
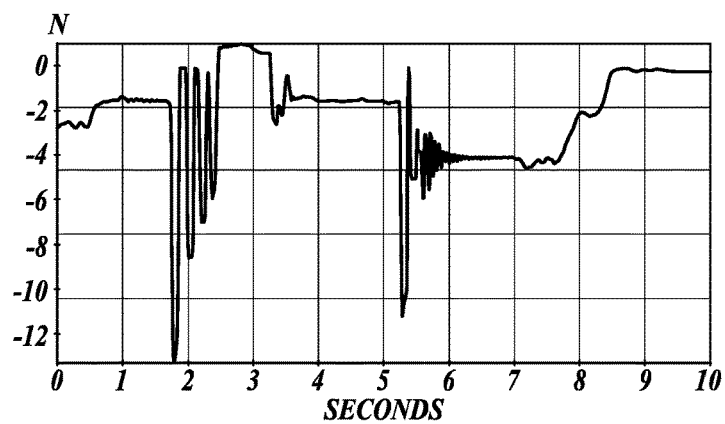
Figure 10C:
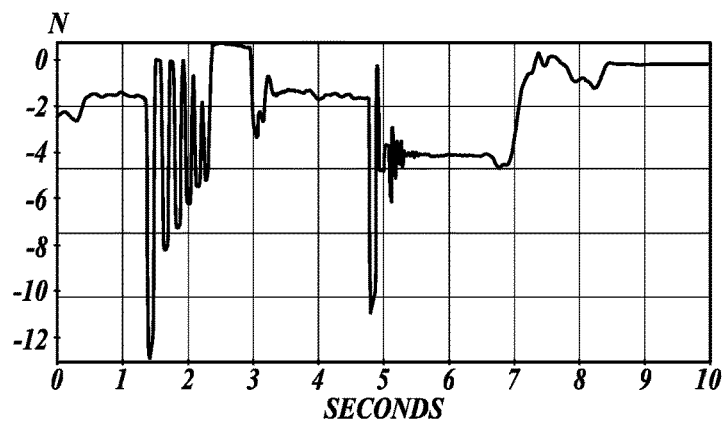

As an example, the oscillating curve or signal for each workpiece referenced in FIGS. 10A-10C decays (gets smaller over time). The damping ratio can be calculated for each workpiece to describe the way in which the signal decays, which is proportional to the material properties of the workpiece.

The damping ratio can be calculated by taking the amplitude ratio of two successive positive peaks as the oscillating signal or curve is decaying, and performing further calculations known to those of ordinary skill in the art. For example, the damping ratio was calculated for a workpiece as follows.

First, the logarithmic decrement is calculated:

$$\delta \triangleq \ln\frac{x1}{x2}$$

x1=0.75 (positive amplitude of a peak)
x2=0.35 (positive amplitude of the next peak)
Using the above calculation, the logarithmic decrement ($\delta$) is equal to 0.76214.

The damping ratio is then calculated:

$$\zeta = \frac{\delta}{\sqrt{(2\pi)^2 + \delta^2}}$$

Using the above calculation, the damping ratio ($\zeta$) was calculated to be 0.12042.

The above calculations are exemplary for one workpiece. It should be appreciated that calculations may be made for both workpieces, i.e., the first, soft viscoelastic workpiece and the second, stiff or hard viscoelastic workpiece. The calculated damping ratios for the first, soft viscoelastic workpiece may be used as criteria for identifying normal chicken breasts or other similar viscoelastic material. Likewise, the calculated damping ratios for the second, stiffer viscoelastic workpiece may be used as criteria for identifying woody chicken breasts or other similar viscoelastic material.

Figure 11A:
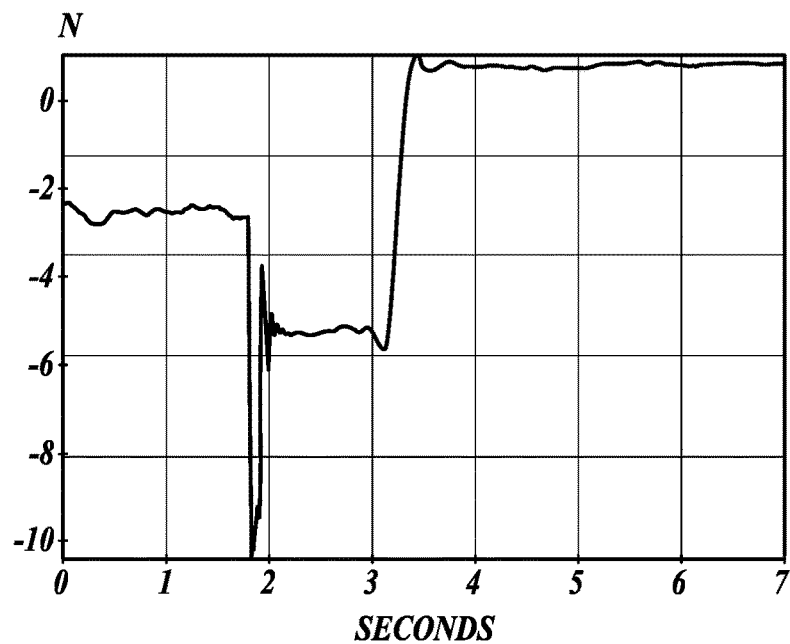
FIG. 11A is graphical results of time dependent strain (Force (Newtons) versus Time (Seconds)) in a third tested workpiece of the experiment.

In further aspects of the experiment, a normal chicken breast was tested to compare the response curve to that of the first, soft viscoelastic workpiece. The results are shown in FIG. 11A. As can be seen, the response curve of a normal chicken breast is similar to the first, soft viscoelastic workpiece.

Figure 11B:
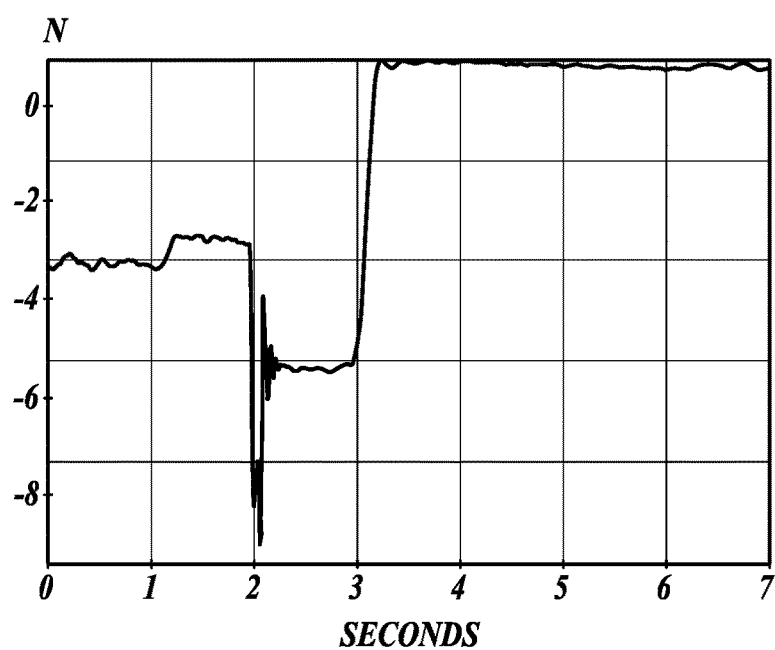
FIG. 11B is graphical results of time dependent strain (Force (Newtons) versus Time (Seconds)) in a fourth tested workpiece of the experiment.

In yet further aspects of the experiment, the inventors found that the use of high impact energy (with a high position of the slide hammer 418) and a small end effector 420 permanently damaged the workpiece during the impact test. By lowering the initial position of the slide hammer 418 to half the height and using a larger diameter end effector, the workpiece was not damaged. Moreover, the response curve, which is shown in FIG. 11B, produced similar results.

Overall Systems of the Exemplary Embodiments of FIGS. 12-15

Figure 12:
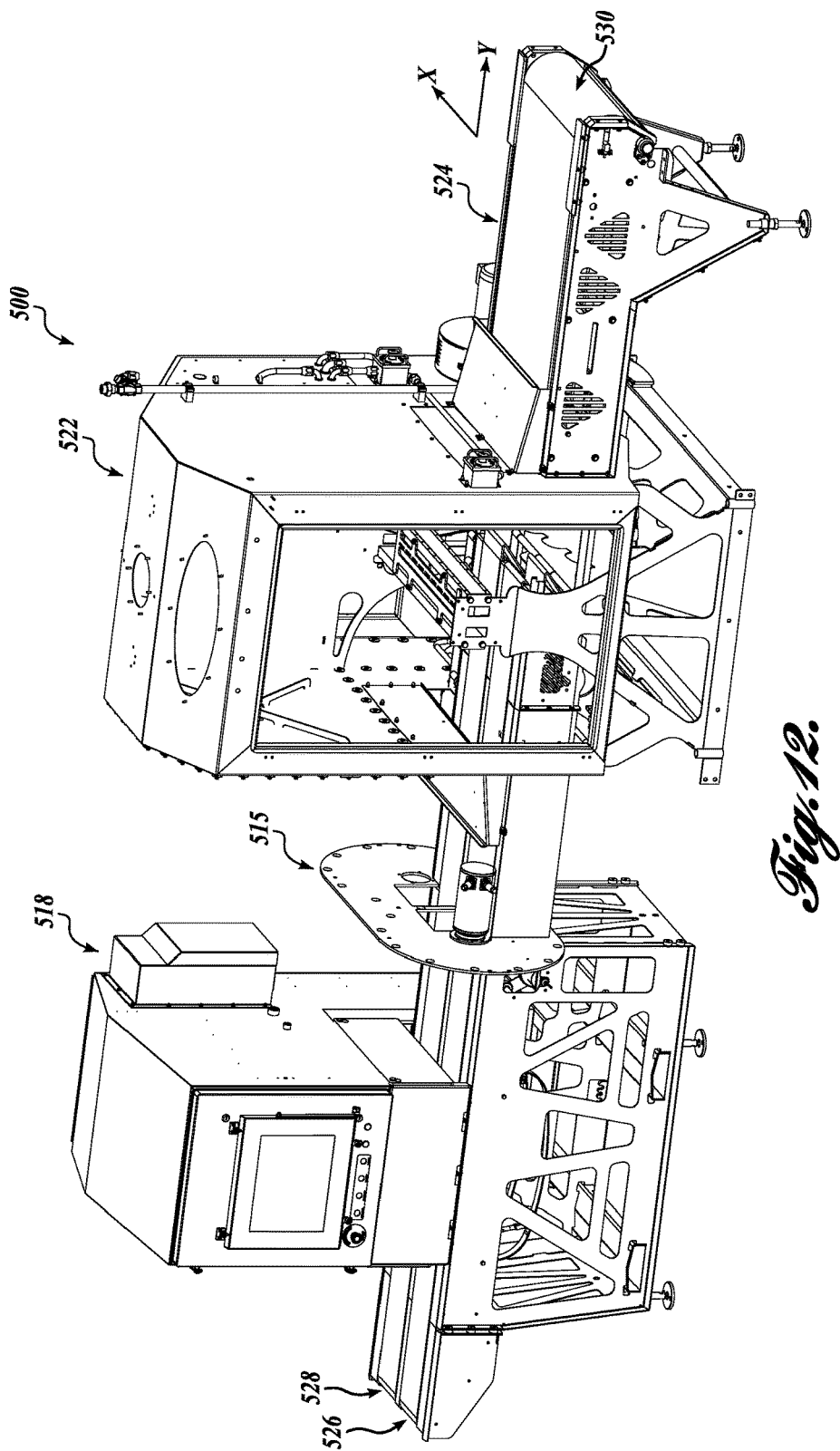
FIG. 12 is an isometric view of an alternative exemplary embodiment of a system formed in accordance with the present disclosure that is configured for measuring physical attributes of workpieces in motion, and optionally cutting and/or optionally unloading the workpieces or portions.

FIG. 12 illustrates another exemplary embodiment of a system 500 for assessing the physical attributes of a workpiece, and optionally scanning, cutting, sorting, unloading, harvesting, etc., the workpieces and/or workpiece portions, in a continuous flow process. However, unlike the systems 100, 100A, and 100B, the system 500 is configured to assess the physical attributes of a workpiece with a fixed measurement assembly 515 (i.e., the measurement assembly 515 does not need to be moved to the workpiece on a carriage or the like). The workpieces may be a food product, such as meat, poultry, or fish. Other types of workpieces may include items composed of, for example, fabric, rubber, cardboard, plastic, wood or other types of material.

In the following description, various alternative system embodiments are described. In that regard, the alternative systems and their corresponding assemblies, apparatus and units are identified by the same part number, but with an alpha suffix. Specifically, exemplary alternative systems 500A and 500B will be described with reference to FIGS. 13, 14, and 15. The descriptions of the parts/components of such system assemblies, apparatus and units that are the same or similar to system 500 are not repeated so as to avoid redundancy in the present disclosure. Moreover, it should be appreciated that any assembly, apparatus, unit, and/or component of systems 500, 500A, and 500B may be used with any other system. Furthermore, aspects of the systems 100, 100A, and 100B (such as the scanning system 110, the cutting assembly 122, the conveyance assembly 102, the unloading assembly 132, etc.) described above may be used or combined with any of the systems 500, 500A, and 500B.

Aspects of the system 500 of FIG. 12 will now be described. The system 500 includes a measurement assembly 515 for assessing the physical attributes of a workpiece, an optional scanning and control assembly 518, an optional cutting assembly 522, an optional sorting assembly 540 (see FIGS. 14 and 15), and a conveyance assembly 524 for processing one or more workpieces (such as workpieces 504 shown in FIG. 15). An optional unloading assembly and/or harvesting assembly (not shown) may be positioned downstream of the cutting assembly 522 or sorting assembly 540.

Unlike the systems 100, 100A, and 100B, the system 500 is configured to assess the physical attributes of a workpiece with a measurement assembly 515 that may be fixed relative to the conveyance assembly 524. In other words, the measurement assembly 515 does not need to move relative to the conveyance assembly 524 in the x-, y-, or z-directions on a carriage or the like in order to test the workpiece. Rather, the measurement assembly 515 may assess the physical attributes of a workpiece while remaining fixed in its position, with the workpieces moving along the longitudinal axis (the y-axis) of the conveyance assembly 524. In that regard, each workpiece may be tested at one or more y-axis locations along the workpiece as it moves along the conveyance assembly 524.

In the illustrated embodiment, additional processing assemblies of the system 500 may be fixed relative to the conveyance assembly 524 as well. For instance, the optional scanning and control assembly 518, the optional cutting assembly 522, the optional sorting assembly 540, the optional unloading assembly, and/or the optional harvesting assembly may be also fixed relative to the conveyance assembly 524 for processing the workpiece. Although the measurement assembly 515 and the optional assemblies of the system 500 are hereinafter described as being configured to test or process a workpiece in a fixed position relative to the conveyance assembly 524, it should be appreciated that one or more of the assemblies may be movable on a carriage or the like relative to the conveyance assembly 524, as set forth above with respect to systems 100, 100A, and 100B. Accordingly, the descriptions and illustrations provided herein should not be seen as limiting.

The optional scanning and control assembly 518 will first be described in detail. The optional scanning and control assembly 518 encloses or at least partially covers an upstream portion of the conveyance assembly 524 for scanning workpieces as they enter the conveyance assembly 524. The optional scanning and control assembly 518 includes one or more scanners that may function similar to the scanners 110 described above, and will therefore only be generally described. The scanner gathers preliminary information and data about the workpieces, such as the position of the workpieces on the conveyance assembly 524, and the physical characteristics of the workpiece, including, for example, shape, thickness, width, volume, length, etc. Using this preliminary information, the scanners may identify an area of interest(s) (one or more y-axis locations) on the workpiece for further assessing the physical attributes of the workpiece with the measurement assembly 515. The data and information gathered by the scanner may be used to determine subsequent processing steps, if any, for the workpiece.

The optional scanning and control assembly 518 further includes a computer or processor (not shown) for processing the data from the scanner to physically characterize the workpieces (shape, width, thickness, length, weight, weight distribution, etc.) such that subsequent processing steps, if any, may be determined for the workpiece. Subsequent processing steps may include, for instance, measuring, sorting, cutting, trimming, portioning, unloading, harvesting, etc. As a specific example, the processor may determine an area of interest on the workpiece (i.e., a y-axis location suitable to test physical properties of the workpiece) and where to make the cuts on the workpieces to achieve the desired size(s)/weight(s) for the portioned pieces. The processor may include one or more input devices (keyboard, mouse, touchpad, etc.) and output devices (monitor, printer, etc.) for interfacing with the processor.

A controller (which can be part of the processor) is provided for controlling the operation of the optional scanning and control assembly 518, the measurement assembly 515, the optional cutting assembly 522, the conveyance assembly 524, and the optional unloading and/or harvesting system. Rather than using a single processor or controller, one or more of the conveyor systems, scanners, measurement assemblies, cutting assemblies, and/or unloading/harvesting assemblies may utilize its own processor or controller. Also, the processor/controller may be connected to a network that ties system 500 to other aspects of the processing, such as downstream processing of the workpieces or workpiece portions.

The measurement assembly 515, which will be described in greater detail below, is generally configured for assessing physical attributes of the workpieces. The measurement assembly 515 may measure the workpiece at the area of interest(s) (such as a y-axis location) identified by the optional scanning and control assembly 518. Any suitable property of the workpiece may be measured, such as its viscoelastic properties (i.e., tenderness, resilience, stiffness, texture, etc., collectively referred to as "viscoelastic properties"), its temperature, etc. The controller of the optional scanning and control assembly 518 may determine subsequent processing steps, if any of the workpiece based upon the measured properties of the workpiece.

For instance, the workpiece may be optionally cut, purposefully left uncut, trimmed, and/or portioned based upon its measured properties by one or more optional cutting assemblies (hereinafter sometimes described as "processing by the cutting assembly"). Any suitable cutting assembly may be used for processing the workpieces. In the embodiment depicted in FIG. 12, the cutting assembly 522 is a waterjet portioning assembly. Any suitable waterjet portioning system may be used, such as a DSI waterjet portioning assembly available from John Bean Technologies Corporation. In that regard, the cutting assembly 522 may be substantially similar to the cutting assembly 122 described above.

Figure 13:
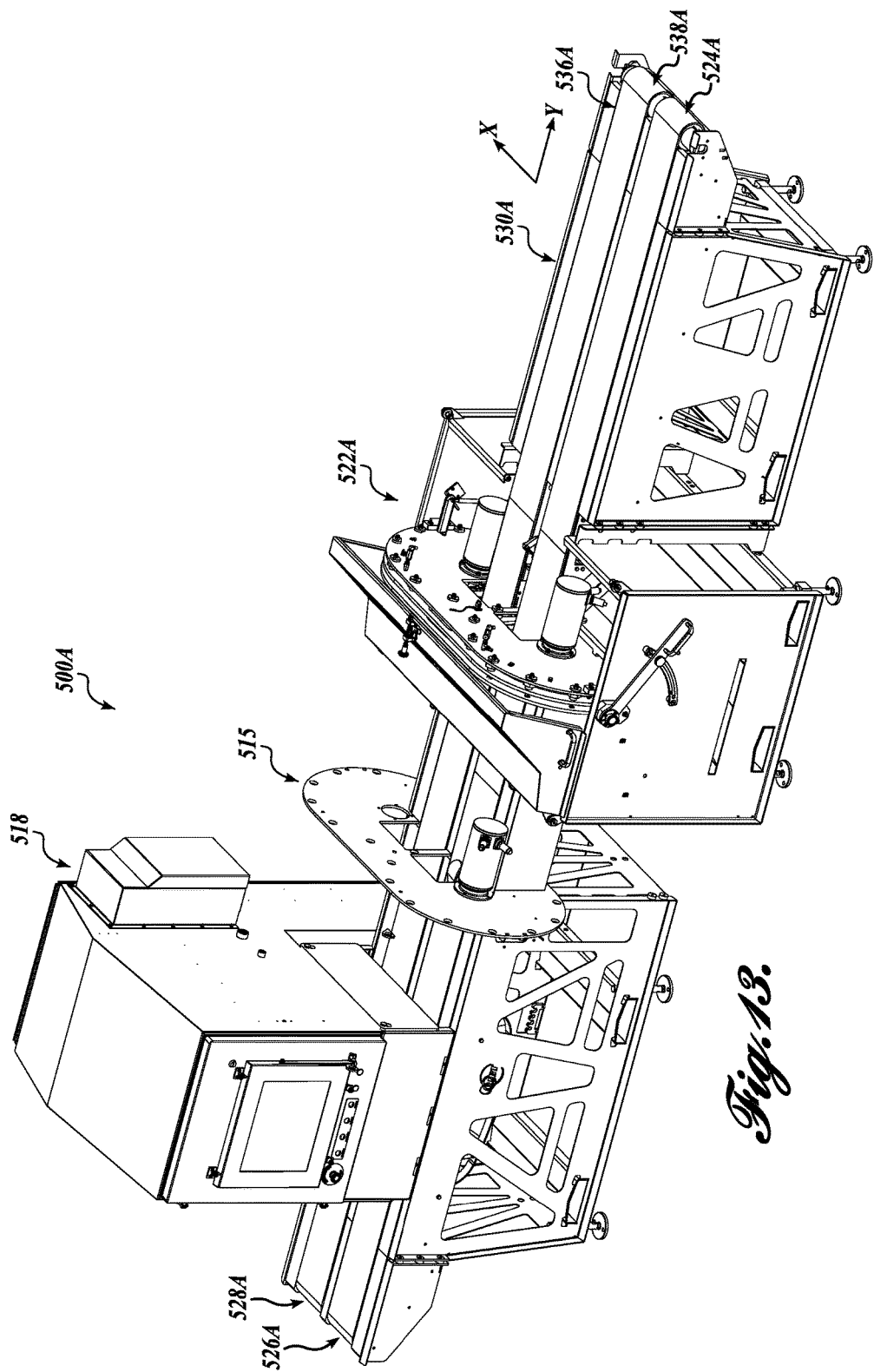
FIG. 13 is an isometric view of another alternative exemplary embodiment of a system formed in accordance with the present disclosure that is configured for measuring physical attributes of workpieces in motion, and optionally cutting and/or optionally unloading or otherwise sorting the workpieces or portions.

In the embodiment depicted in FIG. 13, the cutting assembly 522A is a rotary blade portioner assembly having at least a first rotary blade movable within a housing, wherein the first rotary blade is movable about a first blade axes define by a drive shaft of a motor or other suitable movement device (not labeled). The first rotary blade is positioned substantially transverse to a longitudinal axis of the conveyance assembly 524 such that it may cut (either vertically or at an angle) through a workpiece as it moves along the conveyance assembly 524. Any suitable rotary blade portion assembly may be used, such as the blade portioner assembly shown and described in U.S. patent application Ser. No. 15/004,912, filed on Jan. 23, 2016, entitled "Automatic Gap Adjustment Assembly for Blade Portioner Conveyors", the disclosure of which is hereby expressly incorporated by reference herein, and/or the DSI DB20 blade portioning system available from John Bean Technologies Corporation.

As can be seen in FIGS. 12 and 13, the cutting assemblies 522 and 522A may partially enclose and provide support for the conveyance assembly 524 or 524A. The conveyance assemblies 524 and 524A may be any suitable single, dual, or multiple lane endless conveyor belt assembly suitable for conveying workpieces to be scanned, tested, portioned, unloaded, harvested, or otherwise processed. In that regard, the conveyance assemblies 524 and 524A may be substantially similar to the conveyance assembly 124 described above with reference to FIGS. 1 and 2. More specifically, the conveyance assemblies 524 and 524A may generally include at least one conveyor belt driven by a drive motor (not shown), with at least one underlying support member (not shown) over which the conveyor belt(s) may slide and which is sufficiently stiff to substantially eliminate vibrations and other noise during impact testing, and an encoder for tracking the movement and positioning of the conveyor belt as it is moved, as set forth above with respect to the conveyance assembly 124. Therefore, further details of those components will not be provided.

In the depicted embodiment of FIG. 12, the conveyance assembly 524 may include first and second side-by-side infeed conveyor assemblies 526 and 528 for conveying workpieces to be tested, portioned, sorted, etc., in two side-by-side lanes. The workpieces are conveyed toward an outfeed conveyor assembly 530, and cutters of the cutting assembly 522 may cut, portion, or trim the workpieces as they pass from the infeed to outfeed conveyor assemblies. In that regard, first and second conveyor belt gaps, which may be optionally adjustable, are defined between interior noses of the first and second infeed conveyor assemblies 526 and 528 and the outfeed conveyor assembly 530 for allowing any cutting mechanism to pass therethrough. In the alternative, the conveyance assembly 524 may instead be comprised of a single, wide infeed conveyor and the single outfeed conveyor 530.

The conveyance assembly 524A of FIG. 13 is substantially similar to conveyance assembly 524 in that it includes first and second side-by-side infeed conveyor assemblies 526A and 528A and an outfeed conveyor assembly 530A. However, the outfeed conveyor assembly 530A is shown having first and second side-by-side outfeed conveyor assemblies 536A and 538A. The conveyance assembly 524B of FIG. 14 is substantially similar to conveyance assembly 524 in that it includes first and second side-by-side infeed conveyor assemblies 526B and 528B; however, no outfeed conveyor assembly is provided.

It should be appreciated that any suitable conveyance assembly may be used for the intended application. For instance, in some embodiments, only a single conveyor assembly, rather than two continuous side-by-side conveyor assemblies, may be used. The layout of the conveyance assembly may depend on the processing steps of the workpiece, such as cutting, portioning, trimming, sorting, unloading, etc. As a specific example, a conveyance assembly having an infeed assembly and an outfeed assembly (with a gap defined therebetween) may be desired in a system using a cutting assembly to cut, portion, and/or trim the workpieces. However, in other embodiments, such as in the system 500B of FIG. 14, only an infeed assembly is shown since the workpieces are simply tested by the measurement assembly 515 and then sorted by an optional sorting assembly 540.

Figure 14:
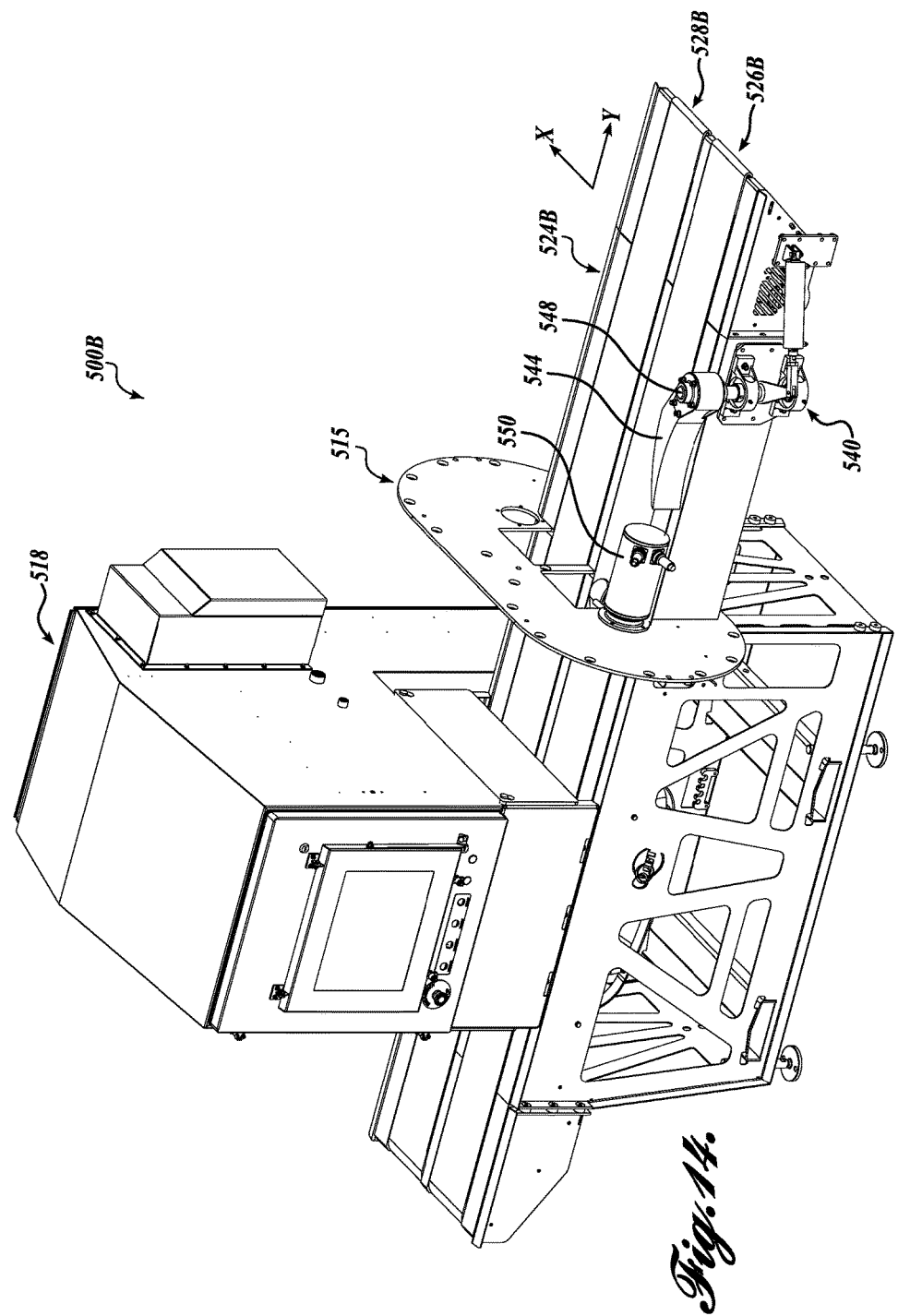
FIG. 14 is an isometric view of yet another alternative exemplary embodiment of a system formed in accordance with the present disclosure that is configured for measuring physical attributes of workpieces in motion, and optionally sorting and/or optionally unloading or otherwise sorting the workpieces or portions.
Figure 15:
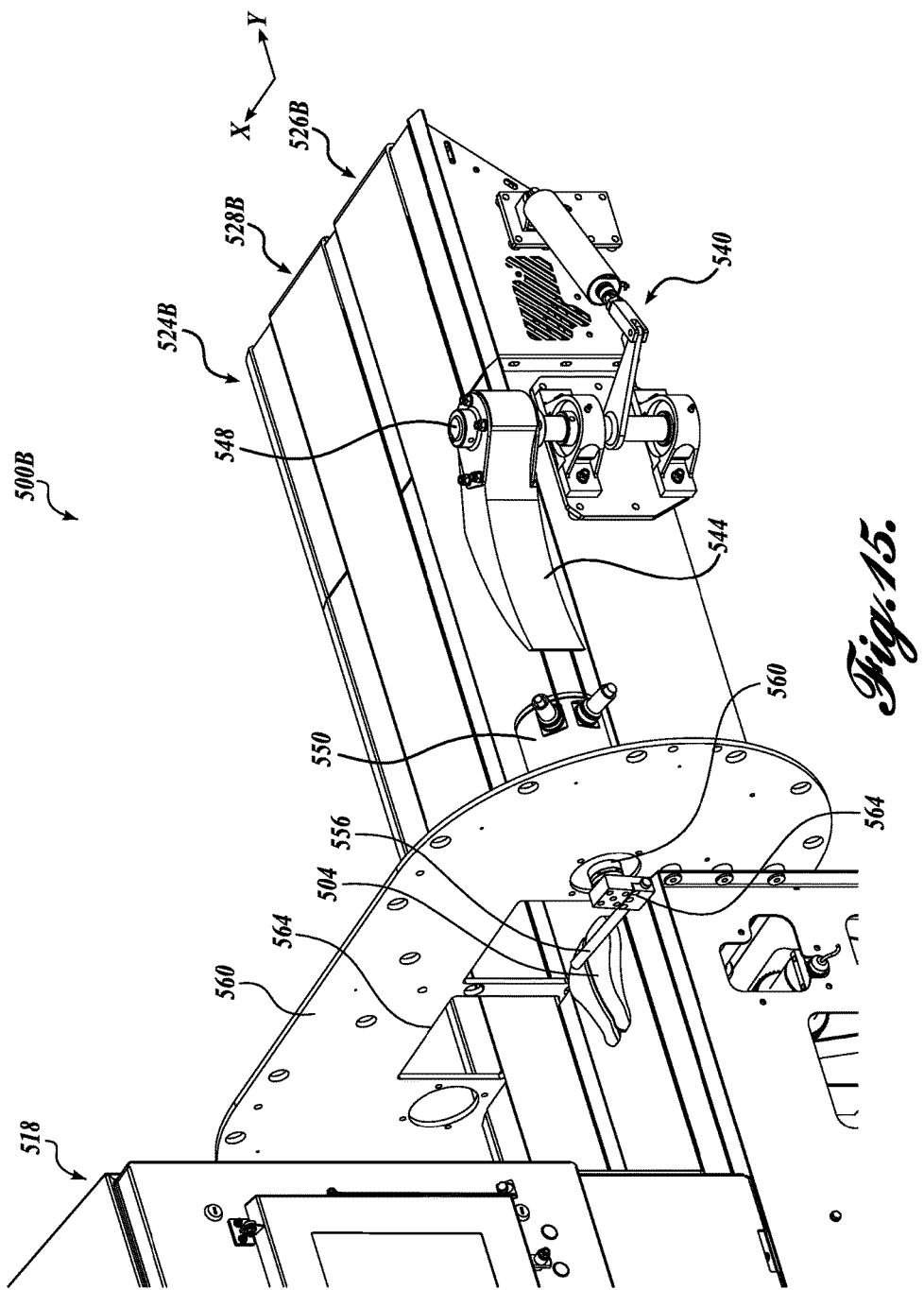
FIG. 15 is an isometric view of the measurement assembly of FIG. 14, showing the physical attributes of a workpiece being measured while the workpiece is in motion.
Figure 16:
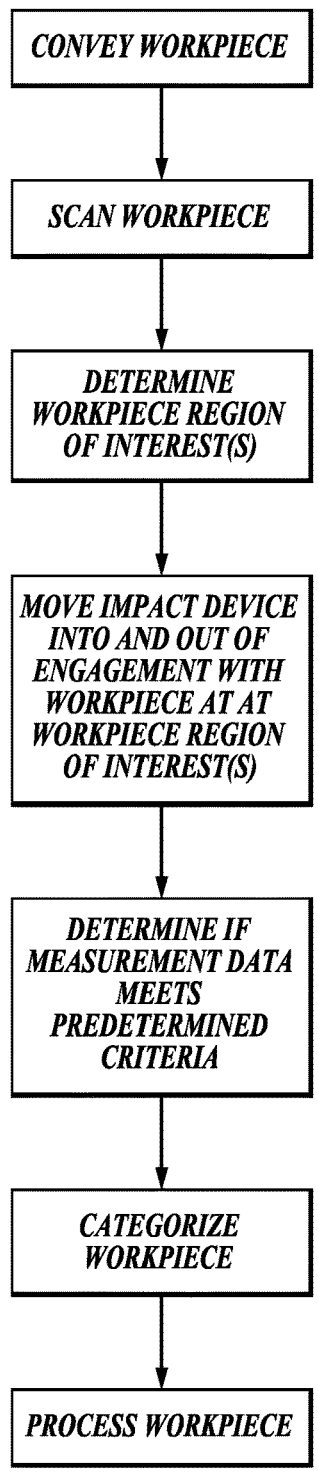
FIG. 16 is a flow chart depicting a method formed in accordance with an exemplary embodiment of the present disclosure.

The optional sorting assembly 540, as shown in FIG. 14 and additionally in FIG. 15, may be any suitable assembly configured to move selected workpieces (based on their measured physical properties, their portion size, etc.) off of the conveyance assembly 524B to another location (such as a bin, a subsequent conveyance assembly, etc.) In the depicted embodiment, the optional sorting assembly 540 comprises an arm 544 pivotal about an arm axis 548 that is substantially transverse to the longitudinal axis of the conveyance assembly 524. The arm 544 reciprocates about the arm axis 548 (through a motor, actuator, or otherwise) to capture and move workpieces off the conveyance assembly 524. In that regard, the arm 544 may be curved or substantially crescent-shaped to help guide workpieces toward an outer edge of the conveyance assembly 524 as they are moved along the conveyance assembly 524.

It should be appreciated that any other suitable sorting assembly may instead be used. Moreover, the sorting assembly 540 may be used with any of the other systems 500 and 500A. In that regard, the sorting assembly 540 may be positioned along the conveyance assembly 524 or 524A either before or after the cutting assembly 522 or 522A, respectively, or at any other desired location along the conveyance assembly 524 or 524A.

In addition to or in lieu of the optional sorting assembly 540, the systems 500, 500A, and/or 500B may include one or more optional unloading assemblies (not shown). In other words, after the workpieces are scanned, measured, optionally sorted and optionally cut, trimmed, and/or portioned, the workpieces may be optionally unloaded from the conveyance assembly 524, 524A, or 524B by one or more unloading assemblies. The optional unloading assemblies may pick up cut or whole workpiece portions from the conveyance assembly 524, 524A, or 524B and transfer the portions or pieces to takeaway locations, which could include optional side conveyors, chutes, or other locations away from the conveyance system. Alternatively, the optional unloading assemblies may pick up portioned workpieces so that the remaining workpiece trim can be removed, and then replace the portioned workpieces onto the conveyance system at a location closely corresponding to the location from which the portioned workpieces were initially picked up by the unloading system.

Any suitable unloading assembly may be used, such as an unloading assembly similar to unloading assembly 132 described above. However, in the systems 500, 500A, and/or 500B, the unloading assembly need not necessarily be secured on a movable carriage. Moreover, the unloading assemblies may be used for any suitable purpose, and they may be positioned along the conveyance assembly 524, 524A, or 524B either before or after the cutting assembly or before or after the sorting assembly, or at any other desired location along the conveyance assembly.

In addition to or in lieu of the optional sorting assembly 540 and/or the optional unloading assembly, the systems 500, 500A, and/or 500B may include one or more optional harvesting assemblies (not shown). The optional harvesting assembly may be an assembly suitable for separating, moving, or guiding workpieces at the outfeed assembly into one of the side-by-side conveyors, into designated bins, onto additional conveyors for further processing, etc. In some embodiments, the harvesting assembly may be automated through a robotic structure or otherwise, and in other embodiments, the harvesting assembly may be comprised of one or more persons manually handling the workpieces based on visual differences. For instance, in one embodiment, the cutting assembly 522 (or 522A) may only cut workpieces having a physical property (measured by the measurement assembly 515) meeting predetermined criteria. In such an embodiment, the harvesting assembly or manual process may remove only unportioned or uncut workpieces, or the harvesting assembly may move the whole workpieces to a first location and the portioned or cut pieces to a second location.

As noted above, any suitable combination of assemblies, units, components, etc. of each of the systems 500, 500A, and 500B (as well as systems 100, 100A, and 100B) may be used for the intended application. For instance, some embodiments may include only a scanning and control assembly, a measurement assembly and an unloading assembly in relation to the conveyance assembly. In other embodiments, the system may include all or most of the assemblies, such as a scanning and control assembly, a measurement assembly, a cutting assembly, a sorting assembly, and an unloading and/or harvesting assembly. Moreover, the order in which the assemblies are positioned along the conveyance assembly may be rearranged as desired. For instance, and as will become further apparent from the discussion below, in some embodiments the system will include a sorting assembly positioned after a measurement assembly, but before a cutting assembly. Thus, the embodiments shown and described herein should not be seen as limiting.

Measurement Assembly

The measurement assembly 515 suitable for measuring physical attributes of a workpiece conveyed along any of the systems 500, 500A, or 500B, or any other suitable system, will now be described in detail. The measurement assembly 515 is similar to measurement assembly 115 in that it is configured to measure physical properties of a workpiece 504 at one or more regions of interest as the workpiece 504 is moving along the conveyance assembly 524, 524A, or 524B. However, as noted above, the measurement assembly 515 may measure the workpiece in motion while remaining in a fixed position relative to the conveyance assembly 524, 524A, or 524B.

In the embodiment depicted in FIG. 15, the measurement assembly 515 is shown measuring physical properties of a piece of chicken as it is moved along the conveyance assembly 524B. However, as noted above, the measurement assembly 515 may instead be used to test any other suitable workpiece. The measurement assembly 515 is configured to measure the viscoelastic properties (i.e., tenderness, stiffness, resilience, texture, etc.) of the workpiece 504 for assessing the workpiece quality (e.g., woody chicken v. non-woody chicken). In at least one specific embodiment, the measurement assembly 515 measures the force response of the workpiece during deformation as a function of time, or the time dependent strain.

Although the measurement assembly 515 may measure the time dependent strain or other viscoelastic properties in any suitable manner, in an exemplary embodiment, the measurement assembly 515 is configured to deform the workpiece 504 at a known rate in a controlled downward and upward motion over the workpiece region of interest. When engaging and deforming the workpiece, the measurement assembly 515 simultaneously measures the force response of the workpiece using a suitable measurement device, such as an encoder.

The deformation of the workpiece 504 can occur at a constant speed, at a frequency of interest, or at a changing rate of speed, or any combination thereof for a predetermined distance. In one example, the measurement assembly 515 deforms the workpiece 504 at a constant velocity for a predetermined distance, where the predetermined distance is proportional to the thickness of the workpiece. As an example, for a 35 mm thick workpiece, the predetermined distance would be about 7 mm or 7/35=20% compression. For a 12 mm thick workpiece, the predetermined distance would be about 2.4 mm or 2.4/12=20% compression.

It should be appreciated that the measurement assembly 515 may also be configured to measure other or additional physical properties of the workpiece, such as the workpiece temperature or other energy content of the workpiece, to assess workpiece quality and/or to determine subsequent processing steps for the workpiece. Moreover, multiple physical measurements may be taken per work piece at one or more areas of interest. It should be appreciated that certain physical property measurements of the workpiece, such as the workpiece temperature may be taken upstream and separate from the system 500.

The measurement assembly 515 includes wired or wireless means for communicating with the computer of the scanning and control assembly 518 and/or another computer. The computer of the scanning and control assembly 518, for example, may control the measurement assembly 515, and the measurement assembly 515 may send the measurement data to the computer. The measurement data is processed by the computer, which can make decisions about the best use of the workpiece 504 or the population of workpieces. In particular, the computer records the force response of the workpiece, calculates one or more commercially important physical parameters for the identified workpiece at the region of interest, records a result for the workpiece, and optionally makes decisions about the best use of the workpiece or the population of workpieces based upon the measured value or values in comparison to predetermined criteria.

The measurement assembly 515 has a sufficiently fast cycle time such that 100% of the workpieces or a sufficient sample size of the workpieces may be tested in the continuous flow of the system 500. Moreover, it should be appreciated that in some embodiments including multiple conveyor lanes, the measurement assembly 515 may only be used to test some or all of the workpieces in some of the lanes (such as one lane). Regardless, no down time is required to test the workpieces, and quality control is increased. Moreover, the measurement assembly 515 is configured to test the viscoelastic properties of the workpiece without damaging the workpiece. As such, tested workpieces that meet the test criteria are not wasted.

Referring to FIGS. 14-15, an exemplary embodiment of a measurement assembly 515 configured to measure the viscoelastic properties of a workpiece 504 as time dependent strain while remaining fixed relative to the conveyance assembly 524B is depicted. In general, the measurement assembly 515 is embodied as a rotary actuator that is configured to move an impact device between at least a first, non-engaging position and second, engaging position for deforming and measuring the deformation in the workpiece 504.

In the depicted embodiment, the impact device is a rod 556 that is movable into and out of engagement with the workpiece 504 for deforming and measuring bounceback of the workpiece while minimizing damage or movement to the workpiece. The rod 556 is generally elongated and cylindrical in shape and positioned to extend along a selected y-axis of the conveyance assembly 524. The rod 556 has a sufficient length to extend (along the y-axis) across at least a portion of the workpiece for impacting and deforming the workpiece. Moreover, the rod 556 is comprised of a suitable stiff and sterile material for deforming the workpiece without adversely affecting the quality of the workpiece, such as stainless steel. It should be appreciated that any other suitable impact device configured to deform the workpiece for producing relevant bounceback data or other data while minimizing damage or movement to the workpiece may instead be used. For instance, the impact device may instead be curved to generally correspond to the shape of the workpiece. Moreover, the rod 556 may instead be positioned along another axis of the conveyance assembly other than the y-axis.

The impact device may include an energy sensor, such as a temperature sensor to detect the temperature of the workpiece when it engages the workpiece 104. The temperature or other energy reading may be processed by the computer of the scanning and control assembly 518 or another suitable computer and taken into account in assessing the viscoelastic properties of the workpiece 504. For instance, a chicken breast at a low temperature below the latent zone may be very stiff and firm (greater than 0% ice crystals), but the chicken breast may not otherwise qualify as "woody chicken."

The rod 556 or other suitable impact device is selectively movable between the engaged and non-engaged positions in a controlled manner by a suitable rotary actuator, such as a rotary servo motor 550. In that regard, the servo motor 550 includes an output shaft 560 that is selectively driven or rotated about its axis in a manner well known in the art. The rod 556 is coupled to the output shaft 560 of the servo motor 550 through a suitable mounting assembly 564. More specifically, the mounting assembly 564 secures the rod 556 to the output shaft 560 such that the rod 556 is substantially transverse to the axis of the output shaft 560 and substantially transverse to the longitudinal x-axis of the conveyance assembly 524B. In this manner, the rod 556 can engage and deform the workpiece 504 at one or more y-axis locations along the workpiece, as may be determined by the size, shape, volume, etc. of the workpiece when scanned by the scanner.

The servo motor 550 is also configured to control the movement of the rod 556 and sense the positional feedback of the rod 556 when it engages and deforms the workpiece 504. In that regard, the servo motor 550 is in communication with or includes a servo motor controller (not shown) for controlling the movement of the rod 556. The servo motor controller may be integral to the servo motor 550 or it may instead be in wired or wireless communication with the servo motor 550. The servo motor controller allows for precise control of the angular position, velocity, and acceleration of the rod 556. More specifically, the servo motor controller moves the rod 556 at a specified velocity, it accelerates and decelerates the rod 556, it stops the movement of the rod 556, it reverses the direction of the rod 556 or allows reversal of the rod (for instance, during bounce back), etc., to appropriately engage and measure a physical property of the workpiece.

To carry out this function, the servo motor controller may be in wired or wireless communication with the computer of the scanning and control assembly 518. The computer may, optionally based upon one or more preliminary workpiece physical parameters determined by the scanning and control assembly 518, send instructions the servo motor controller to move the rod 556 into engagement with one of more areas of interest of the workpiece. For example, the most relevant viscoelastic measurement may need to be taken at the thickest cross-sectional portion of the workpiece. The computer instructs the controller to take measurements of the workpiece at a predetermined location (e.g, a specific y-axis location) in a specified manner (e.g., at a specified velocity, acceleration, etc.).

Once the measurements are taken, the servo motor controller may send the measurement data to the computer for further processing to determine what, if any, next processing steps should be taken with respect to the measured workpiece. In particular, the computer records the force response of the workpiece, calculates one or more commercially important physical parameters for the identified workpiece at the region of interest, optionally records a result for the workpiece, and optionally makes decisions about the best use of the workpiece or the population of workpieces based upon the measured value or values in comparison to predetermined criteria.

As noted above, the measurement assembly 515 may measure the force response of the workpiece using a suitable measurement device, such as an optical rotary encoder or another suitable precision feedback measurement device (not shown). The rotary encoder or other measurement device may be in communication with the servo motor 550 or may otherwise define a component of the servo motor 550. In any event, the rotary encoder or other measurement device is configured to provide positional feedback of the rod 556 as it is moved by the controller and as it engages and bounces back from the workpiece 504. In particular, the encoder is configured to detect the position of the rod 556 (i.e., its angular position relative to the workpiece) as well as any bounceback of the rod 556 (or the force response of the workpiece) after it engages and deforms the workpiece 504. The encoder or other suitable measurement device is in communication with the servo motor controller such that the servo motor controller may send the measurement data to the computer for further processing, as discussed above.

The servo motor 550 and rod 556 may be positioned relative to the conveyance assembly 524B in any suitable manner such that the rod 556 may impact the workpiece 504 as it moves along the conveyance assembly 524B. For instance, and as shown in FIG. 15, the measurement assembly 515 may include a housing 560 that is secured to side portions of the conveyance assembly 524B and extends across the conveyance assembly 524B (in the y-axis direction). The servo motor 550 may be secured to the housing 560 in a suitable manner (such as with mounting brackets) such that the rod 556 may extend across at least a portion of the conveyance assembly 524B when moved into the engaged position. In that regard, the housing 560 may include one or more openings 564 for allowing a conveyor belt with workpieces to pass therethrough. It should be appreciated that the servo motor 550 and rod 556 may instead be positioned relative to the conveyance assembly 524B with a movable carrier unit having a carriage, such as carriage 180, or the like. In such an alternative configuration, the carriage could be moved into a desired location to accommodate different types of workpieces or different types of testing.

General Operation of the Exemplary Embodiments of FIGS. 12-15

The general operation of the systems 500, 500A, and 500B will now be described. Initially, the scanners of the scanning and control assembly 518 optionally scan the workpieces to produce scanning information representative of the workpieces, and the scanners forward the scanning information to the processor/computer of the scanning and control assembly 518. The processor/computer, using a scanning program, analyzes the scanning data to determine the location of the workpieces on the conveyance assembly 524, 524A, or 524B.

The processor/computer also develops a length, width, area, thickness, and/or volume profile of the scanned workpiece. The processor/computer can then model the workpiece to determine how it may be efficiently measured. For instance, the processor/computer can run measurement software to determine how to measure the time dependent strain, shape, area, weight, temperature, and/or thickness of the workpiece, or other physical properties. As a specific example, with the thickness of the workpiece known, efficient and rapid determination of time dependent strain or other similar measurements may be made with the measurement assembly 115.

The processor/computer also determines one or more workpiece regions of interest for making a physical attribute measurement. In the specific embodiments of FIGS. 12-15, the workpiece regions of interest are defined as one or more y-axis locations along the conveyance assembly 524, 524A, or 524B. In this manner, the impact device or rod 556 of the measurement assembly 515 may be moved into engagement with the workpiece at the selected y-axis location for testing the workpiece without necessitating movement of the measurement assembly 515. It should be appreciated that in alternative embodiments of the measurement assembly 515 having a different impact device, the workpiece region of interest may instead be at a selected x- and y-axis location along the conveyance assembly. Moreover, the processor/computer may compute several areas of interest for making several measurements per workpiece.

Using the workpiece data, the processor/computer functions as a controller to activate the measurement assembly 115 and instruct the servo motor 550 to move the rod 556 at a specified velocity, force, and/or acceleration to impact the workpiece region of interest. The servo motor 550 moves the rod 556 into engagement with the workpiece to take one or more measurements for assessing the physical attributes of the workpiece, such as its viscoelastic properties. The measurement data is processed by the processor/computer, which can make decisions about the best use of the workpiece or the population of workpieces by comparing the measurement data to predetermined criteria. Measurement data or criteria similar to that described above with reference to FIGS. 10A-10C may be used for assessing the viscoelastic properties of the workpiece (e.g., a "woody" piece of chicken vs. a "non-woody" piece of chicken).

The processor/computer of the scanning and control assembly 518, using the scanning program and/or an optional portioning program, may also model the workpiece to determine how it should be sorted, divided, trimmed, and/or cut into pieces composed of specific visual and physical attributes. In that regard, the processor/computer may function as a controller to control the optional cutter assembly 520 to cut the workpieces according to selected criteria, to control the optional sorting assembly 540 to sort or remove selected workpieces from the conveyance assembly, and to control the optional unloading and/or harvesting assembly for at least temporarily removing the workpieces or workpiece portions from the conveyance assembly.

As discussed above, the assemblies of the system 500, 500A, and/or 500B may be used in any order along the length of the conveyance assembly, in any combination. For example, the system may be configured to scan the workpiece to gather data and determine a region of interest(s), measure one or more properties (such as the viscoelastic properties) of the workpiece at the region of interest(s), and report the measured properties to the scanning and control assembly 518. As another example, the system may be configured to scan the workpiece to gather data and determine a region of interest(s), measure one or more properties (such as the viscoelastic properties) of the workpiece at the region of interest(s), report the measured properties to the scanning and control assembly 518, and based on the measured properties of the workpiece and comparison to predetermined criteria, remove the workpiece (e.g, a "woody" piece of chicken) from the conveyance assembly with the sorting assembly 540 or leave the workpiece (e.g, a "non-woody" piece of chicken) on the conveyance assembly for further processing. The additional processing of the remaining workpieces (e.g, a "non-woody" piece of chicken) may include cutting, trimming, portioning, etc. the workpieces with the cutting assembly 522 or 522A or another suitable assembly, and/or unloading and/or harvesting the workpieces.

As yet another example, the system may be configured to scan the workpiece to gather data and determine a region of interest(s), measure one or more properties (such as the viscoelastic properties) of the workpiece at the region of interest(s), report the measured properties to the scanning and control assembly 518, and based on the measured properties of the workpiece and comparison to predetermined criteria, cut, trim, or portion only selected workpieces (e.g., a "non-woody" piece of chicken) with a cutting assembly 522 or 522A. In such a system configuration, the uncut workpieces (e.g, a "woody" piece of chicken) left on the conveyance assembly can be removed by a sorting assembly 540, an unloading assembly, or a harvesting assembly. In the event that the harvesting assembly comprises one or more persons, the persons could be trained to remove only whole workpieces, knowing that such uncut workpieces included undesirable physical properties (e.g, "woody" chicken).

It should be appreciated that any other suitable configuration may instead be used. For instance, any of the above system configurations may instead be done without recording or reporting measurement data for the workpiece. Moreover, as can be appreciated by referring to FIGS. 12-15, depending on the system configuration, one or more infeed and/or outfeed conveyor assemblies may be needed to carry out certain processing steps, such as cutting.

Thus, while illustrative embodiments have been illustrated and described, it will be appreciated that various changes can be made therein without departing from the spirit and scope of the present disclosure.

The invention claimed is:

1. A system for measuring physical properties of a workpiece in motion, comprising:
   (a) a conveyance assembly for conveying the workpiece;
   (b) a scanning assembly for scanning the workpiece; and
   (c) a measurement assembly for measuring at least one viscoelastic property of the workpiece while the workpiece is in motion, wherein the measurement assembly is a rotary actuator configured to selectively move an impact device into and out of engagement with the workpiece while the workpiece is in motion, wherein the impact device is coupled to an output shaft of the rotary actuator, wherein an axis of the output shaft is substantially transverse to an axis of the impact device, and wherein the axis of the output shaft is substantially parallel to a longitudinal axis of the conveyance assembly.

2. The system according to claim 1, wherein the measurement assembly further comprises a strain gauge.

3. The system according to claim 1, wherein the measurement assembly is configured to test the at least one viscoelastic property of the workpiece without damaging the workpiece.

4. The system according to claim 1, further comprising an unloading assembly operable to remove at least one of whole or cut workpiece portions from the conveyance assembly.

5. The system according to claim 1, further comprising a control system processor operable to process scanning information data and direct the measurement assembly to a workpiece area of interest for measuring the at least one viscoelastic property of the workpiece.

6. The system according to claim 1, further comprising at least one carrier unit for carrying together both a cutting assembly for cutting the workpiece and at least one unloading system to remove the cut portions from the conveyance assembly and place said removed cut portions at selected locations away from the conveyance assembly.

7. The system according to claim 1, further comprising a sorting assembly configured to remove the workpiece from the conveyance assembly after being measured by the measurement assembly.

8. A method of processing a workpiece in motion based on measured physical properties of the workpiece, comprising:
   (a) moving at least one workpiece along a conveyance assembly;
   (b) scanning the at least one workpiece to determine a workpiece region of interest;
   (c) selectively rotating an impact device into and out of engagement with the at least one workpiece at the region of interest while the at least one workpiece is in motion to measure at least one viscoelastic property of the at least one workpiece wherein the impact device is coupled to an output shaft of the rotary actuator, wherein an axis of the output shaft is substantially transverse to an axis of the impact device, and wherein the axis of the output shaft is substantially parallel to a longitudinal axis of the conveyance assembly;
   (d) comparing the measurement data to predetermined criteria; and
   (e) selecting a subsequent processing step for the at least one workpiece based upon said comparison.

9. The method according to claim 8, further comprising measuring the at least one viscoelastic property of the at least one workpiece without damaging the workpiece.

10. The method according to claim 8, wherein the at least one viscoelastic property is time dependent strain.

11. The method according to claim 8, further comprising unloading at least one of whole and cut portions of the at least one workpiece with an unloading assembly.

12. The method according to claim 8, further comprising processing the at least one workpiece with a cutting assembly if the measurement data meets predetermined criteria.

13. The method according to claim 12, further comprising removing the at least one workpiece processed by the cutting assembly with one of a sorting assembly, an unloading assembly, and a harvesting assembly.

14. The method according to claim 12, further comprising removing the at least one workpiece not processed by the cutting assembly with one of a sorting assembly, an unloading assembly, and a harvesting assembly.

15. The method according to claim 8, further comprising removing the at least one workpiece from the conveyance assembly with one of a sorting assembly, an unloading assembly, and a harvesting assembly if the measurement data meets predetermined criteria.

16. A system for measuring physical properties of a workpiece in motion, comprising:
   (a) a conveyance assembly for conveying the workpiece;
   (b) a scanning assembly for scanning the workpiece;
   (c) a measurement assembly for measuring at least one physical property of the workpiece while the workpiece is in motion;
   (d) a first carrier unit for moving the measurement assembly relative to the conveyance assembly to measure the workpiece while the workpiece is in motion; and
   (e) at least a second carrier unit for carrying together both a cutting assembly for cutting the workpiece and at least one unloading system to remove the cut portions from the conveyance assembly and place said removed cut portions at selected locations away from the conveyance assembly.

17. The system according to claim 16, wherein the measurement assembly is a linear servo motor having a shaft vertically oriented relative to the conveyance assembly and moveable toward and away from the conveyance assembly, wherein an end effector is defined on a distal end of the shaft for engaging the workpiece.

18. The system according to claim 1, wherein the rotary actuator is a rotary servo motor having a servo motor controller configured to control at least one of the angular position, velocity, and acceleration of the impact device.

19. The system according to claim 18, further comprising an optical rotary encoder in communication with the servo motor controller that is configured to provide positional feedback of the impact device as it is moved into and out of engagement with the at least one workpiece while the workpiece is in motion.

20. The method according to claim 8, further comprising varying at least one of the angular position, velocity, and acceleration of the impact device to suitable engage and measure the at least one viscoelastic property of the at least one workpiece while the workpiece is in motion.

21. A system for measuring physical properties of a workpiece in motion, comprising:
   (a) a conveyance assembly for conveying the workpiece;
   (b) a scanning assembly for scanning the workpiece; and
   (c) a measurement assembly for measuring at least one viscoelastic property of the workpiece while the workpiece is in motion in multiple measurement motions per workpiece.

22. The system of claim 21, further comprising an actuator configured to move an impact device into and out of engagement with the workpiece without damaging the workpiece.

* * * * *